(12) United States Patent
Huehn et al.

(10) Patent No.: US 10,876,163 B2
(45) Date of Patent: Dec. 29, 2020

(54) DETECTION AND QUALITY CONTROL OF REGULATORY T CELLS THROUGH DNA-METHYLATION ANALYSIS OF THE FOXP3 GENE

(75) Inventors: Jochen Huehn, Berlin (DE); Stefan Floess, Berlin (DE); Alf Hamann, Eichwalde (DE); Sven Olek, Berlin (DE); Udo Baron, Berlin (DE)

(73) Assignees: Epiontis GmbH, Berlin (DE); Charite-Universitatsmedizin Berlin, Berlin (DE)

( * ) Notice: Subject to any disclaimer, the term of this patent is extended or adjusted under 35 U.S.C. 154(b) by 0 days.

(21) Appl. No.: 11/713,240

(22) Filed: Feb. 28, 2007

(65) Prior Publication Data
US 2007/0269823 A1 Nov. 22, 2007

Related U.S. Application Data

(60) Provisional application No. 60/777,631, filed on Feb. 28, 2006.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| | | |
|---|---|---|
| 2003/0068620 A1 | 4/2003 | Markowitz et al. |
| 2003/0082609 A1 | 5/2003 | Olek et al. |
| 2004/0072197 A1* | 4/2004 | Jones et al. .................. 435/6 |
| 2006/0024676 A1 | 2/2006 | Uhlmann et al. |
| 2006/0040288 A1 | 2/2006 | Richardson et al. |
| 2007/0269823 A1 | 11/2007 | Huehn et al. |

FOREIGN PATENT DOCUMENTS

WO   WO 02/090600   11/2002

OTHER PUBLICATIONS stason.org/TULARC/health/articles/Aids-Glossary-R-V.html, printed May 7, 2009).*
Benner et al (Trends in Genetics (2001) vol. 17, pp. 414-418).*
Morgan et al (Human Immunology (2005) vol. 66, pp. 13-20).*
Ehrlich et al. (2002 Oncogene vol. 21 p. 5400).*
Cottrell (Clinical Biochemistry 2004 vol. 37 p. 595).*
Walsh et al (Genes & Development (1999) vol. 13, pp. 26-36).*
May et al (Science (1988) vol. 241, p. 1441).*
Owen et al (Endocirinology Abstracts 2003).*
Wildin ( Journal of autoimmunity (20050 vol. 25, pp. 56-62).*
GenBank Accession NC_000023.8 GI:51511752 (Oct. 25, 2004).*
Buck et al (Biotechniques. Sep. 1999;27(3):528-36).*
NCBI blast af277994 mus musculus scrufin (fox P3 gene) blast. ncbi.nlm.nih.gov/blast.cgi Sep. 19, 2013.*
NCBI blast SEQ ID No. 13 vs maccablast.ncbi.nlm.nih.gov/blast.cgi Oct. 9, 2013.*
NCBI blast SEQ ID No. 17 vs maccablast.ncbi.nlm.nih.gov/blast.cgi Oct. 9, 2013.*
NCBI blast SEQ ID No. 18 vs maccablast.ncbi.nlm.nih.gov/blast.cgi Oct. 9, 2013.*
Herman (Proceeding National Academy of Sciences (1996) vol. 93, pp. 9821-9826).*
Song (Proceeding National Academy of Sciences (2005) vol. 102, pp. 3336-3341).*
Derks (Cellular Oncology (2004) vol. 26, pp. 291-299).*
Bock (Bioinformatics (2005) vol. 21, pp. 4067-4068).*
Warnecke (Methods (2002) vol. 27, pp. 101-107).*
Dupont (Analytical Biochemistry (2004) vol. 333, pp. 119-127).*
Herman (Proc Natl Acad Sci USA (1996) vol. 93, pp. 9821-9826).*
Li (Bioinformations (2002) vol. 18, pp. 1427-1431).*
Qiagen Bood & Tissue handbook (Jul. 2006).*
Floess (PLOS biology (2007) vol. 5, e38, pp. 169-178).*
Lewin et al. "Quantitative DNA methylation analysis based on four-dye trace data from direct sequencing of PCR amplificates" *Bioinformatics*, 2004, pp. 3005-3012, vol. 20.
Mantel et al. "Molecular mechanisms underlying FOXP3 induction in human T cells" *J. Immunol.*, 2006, pp. 3593-3602, vol. 176.
Erlich, M. "Expression of Various Genes is Controlled by DNA Methylation During Mammalian Development" *Journal of Cellular Biochemistry*, 2003, pp. 899-910, vol. 88.
Dieffenbach, C.W. et al. "General concepts for PCR primer design" *PCR Methods Appl.*, 1993, 3:30-37.
Katoh, M. and Katoh, M. "Human *FOX* gene family (Review)" *Int'l J. Oncol.*, 2004, 25:1495-1500.
Roux, K.H. "Optimization and troubleshooting in PCR" *PCR Methods Appl.*, 1995, 4:185-194.
Tra, J. et al. "Infrequent occurrence of age-dependent changes in CpG island methylation as detected by restriction landmark genome scanning" *Mech. Ageing Develop.*, 2002, 123:1487-1503.
NCBI Blast SEQ ID No. 1 (of U.S. Appl. No. 11/713,579) vs *Rattus norvegicus* strain (NC_005120.3), Oct. 15, 2013.
NCBI Blast SEQ ID No. 2 (of U.S. Appl. No. 11/713,579) vs *Rattus norvegicus* strain (NC_005120.3), Oct. 15, 2013.
NCBI Blast *Mus musculus scurfin* (AF277994) vs *Rattus norvegicus* strain (NC_005120.3), Oct. 15, 2013.

(Continued)

*Primary Examiner* — Steven Pohnert

(74) *Attorney, Agent, or Firm* — BakerHostetler

(57) ABSTRACT

The present invention relates to a method, in particular an in vitro method for identifying FoxP3-positive regulatory T cells, preferably CD25$^+$CD4$^+$ regulatory T cells of a mammal, comprising analysing the methylation status of at least one CpG position in the gene foxp3 or an orthologous or paralogous gene thereof, and the use of DNA-methylation analysis of the gene of the transcription factor FoxP3 for a detection and quality assurance and control of regulatory T cells. Furthermore, the present invention relates to a kit for performing the above methods as well as respective uses.

12 Claims, 6 Drawing Sheets
(2 of 6 Drawing Sheet(s) Filed in Color)

Specification includes a Sequence Listing.

(56) References Cited

OTHER PUBLICATIONS

Koiwa, T. et al. "5'-long terminal repeat-selective CpG methylation of latent human T-cell leukemia virus type 1 provirus in vitro and in vivo" *J. Virol.*, 2002, 76(18):9389-9397.
Grunau, C. et al., "Bisulfite genomic sequencing: systematic investigation of critical experimental parameters," *Nucleic Acids Research*, 2001, vol. 29, No. 13, e65.
Accession No. AF277993, "*Homo sapiens* scurfin (FOXP3) mRNA, complete cds" Jan. 24, 2001.
Accession No. DQ010327, "*Homo sapiens* forkhead box P3 (FOXP3) mRNA, complete cds, alternatively spliced" May 10, 2005.
Accession No. NC_000023, "*Homo sapiens* chromosome X, reference assembly, complete sequence" Mar. 3, 2008.
Ansel et al. "An epigenetic view of helper T cell differentiation" *Nature Immunol*, 2003, pp. 616-623, vol. 4.
Antequera etal. "No. Of CpG islands and genes in human and mouse" *Proc Nati Aced Sci USA*, 1993, pp. 11995-11999, vol. 90.
Attwood et al. "DNA methylation and the regulation of gene transcription" *CMLS*, 2002, pp. 241-257, vol. 59.
Bharat etal. "Regulatory T cell-mediated transplantation tolerance" *Immunol Res*, 2005, pp. 195-212, vol. 33, No. 3.
Bird, A. "DNA methylation patterns and epigenetic memory" *Genes and Dev*, 2002, pp. 6-21, vol. 16.
Brunkow et al. "Disruption of a new forkhead/winged-helix protein, scurfin, results in the fatal lymphoproliferative disorder of the scurfy mouse" *Nat. Genet.*, 2001, pp. 68-73, vol. 27, No. 1.
Bruniquel et al. "Selective, stable demethylation of the interleukin-2 gene enhances transcription by an active process" *Nat Immunol.*, 2003, pp. 235-240, vol. 4.
Chen et al. "Impaired Allogeneic Activation arid T-helper 1 Differentiation of Human Cord Blood Naïve CD4 T Cells" *Biol Blood Marrow Transplant*, 2006, pp. 160-171, vol. 12.
Chen et al. "Conversion of Peripheral $CD4^+$ $CD25^-$ Naive T Cells to $CD4^+$ $CD25^+$ Regulatory T Cells by TGF-ß Induction of Transcription Factor Foxp3" *J Exp Med*, 2003, pp. 1875-86, vol. 198, No. 12.
Esteller, M. "CpG island hypermethylation and tumor suppressor genes: a booming present, a brighter future" *Oncogene*, 2002, pp. 5427-5440, vol. 21.
Fantini et al. "Cutting Edge: TGF-ß Induces a Regulatory Phenotype in $CD4^+$ $CD25^-$ T Cells through Foxp3 Induction and Down-Regulation of Smad7" *J Immunol.*, 2004, pp. 5149-5153, vol. 172, No. 9.
Fantini et al. "Transforming growth factor ß induced FoxP3+ regulatory T cells suppress Th1 mediated experimental colitis" *Gut*, 2005, pp. 671-680, vol. 55.
Fontenot et al. "A well adapted regulatory contrivance: regulatory T cell development and the forkhead family transcription factor Foxp3" *Nat Immunol*, 2005, pp. 331-337, vol. 6.
Fu et al. "TGF-b Induces Foxp3+ T-Regulatory Cells from $CD4^+$ $CD25^-$ Precursors" *Am J Transplant*, 2004, pp. 1614-1627, vol. 4, No. 10.
Gavin etal. "Single-cell analysis of normal and FOXP3-mutant human T cells: FOXP3 expression without regulatory T cell development" 2006, pp. 6659-6664, vol. 103.
Huan et al. "Decreased FOXP3 levels in multiple sclerosis patients" *J Neurosci Res.*, 2005, pp. 45-52, vol. 81, No. 1.
Jones etal. "Cancer epigenetics comes of age" *Nature Genetics*, 1999, pp. 163-167, vol. 21.
June et al. "Clinical application of expanded $CD4^+25^+$ cells" *Semin. Immunol.*, 2006, pp. 78-88, vol. 18.
Khazaie et al. "The impact of $CD4^+CD25^+$ Treg on tumor specific $CD8^+$ T cell cytotoxicity and cancer" *Semin Cancer Biol.*, 2006, pp. 124-136, vol. 16, No. 2.
Laird, P. W. "The power and the promise of dna methylation markers" *Nature Reviews/Cancer*, 2003, pp. 253-266, vol. 3.
Lee et al. "Th2 Lineage Commitment and Efficient IL-4 Production Involves Extended Demethylation of the IL-4 Gene" *Immunity*, 2002, pp. 649-660, vol. 16.
Lewin et al. "Quantitative DNA methylation analysis based on four-dye trace data from direct sequencing of PCR amplificates" *Bioinformatics*, pp. 3005-3012, vol. 20.
Li, E. "Chromatin modification and epigenetic reprogramming in mammalian development" *Nature Reviews/Genetics*, 2002, pp. 662-673, vol. 3.
Mantel et al. "Molecular mechanisms underlying FOXP3 induction in human t cells" *J. Immunol.*, pp. 3593-3602, vol. 176.
Morgan et al. "Expression of FOXP3 mRNA is not Confined to $CD4^+CD25^+$T Regulatory Cells in Humans" *Hum Immunol.*, 2005, pp. 13-20, vol. 66.
Olek et al. "A modified and improved method for bisulphite based cytosine methylation analysis" *Nucleic Acid Res*, 1996, pp. 5046-5066, vol. 24.
Park et al. "Acquisition of anergic and suppressive activities in transforming growth factor-ß-costimulated $CD4^+CD25^-$ T cells" *Int. Immunol.*, 2004, pp. 1203-1213, vol. 16, No. 8.
Pillai et al. "Transient regulatory T-cells: A state attained by all activated human T-cells" *Clin Immunol.*, 2006, pp. 18-29, vol. 123.
Roncador et al. "Analysis of FOXP3 protein expression in human $CD4^+CD25^+$ regulatory T cells at the single-cell level" *Eur J Immunol.*, 2005, pp. 1681-1691, vol. 35.
Sakaguchi, S. "Naturally arising Foxp3-expressing $CD25^+$ $CD4^+$ regulatory T cells in immunological tolerance to self and non-self" *Nat Immunol*, 2005, pp. 345-352, vol. 6.
Schmidt-Weber et al. "The Role of the FOXP3 transcription factor in the immune regulation of allergic asthma" *Curr Allergy Asthma Rep*, 2005, pp. 356-361, vol. 5, No. 5.
Walker etal. "Induction of FoxP3 and acquisition of T regulatory activity by stimulated human $CD4^+CD25^-$ T cells" *J Clin. Invesr.*, 2003, pp. 1437-1443, vol. 112.
Wan et al. "Identifying Foxp3-expressing suppressor T cells with a bicistronic reporter" *Proc Natl Acad Sci USA*, 2005, pp. 5126-5131, vol. 102, No. 14.
Wolf et al. "The Expression of the Regulatory TCell-Specific Forkhead Box Transcription Factor FoxP3 is Associated with Poor Prognosis in Ovarian Cancer" *Clin. Cancer Res.*, 2005, pp. 8326-8331, vol. 11, No. 23.
Yagi et al. "Crucial role of FOXP3 in the development and function of human $CD25^+CD4^+$ regulatory T cells" *Int. Immunol.*, 2004, pp. 1643-1656, vol. 16.
Ziegler, S.F. "FOXP3: Of mice and men" *Annu Rev Immunol.*, 2006, pp. 209-226, vol. 24.
Zorn et al. "Reduced frequency of $FOXP3^+$ $CD4^+$ $CD25^+$ regulatory T cells in patients with chronic graft-versus-host disease" *Blood*, 2005, pp. 2903-2911, vol. 106, No. 8.
Baron, U. et al. "DNA demethylation in the human FOXP3 locus discriminates regulatory T cells from activated $FOXP3^+$ conventional T cells" *Eur. J. Immunol.*, 2007, 37:2378-2389.

* cited by examiner

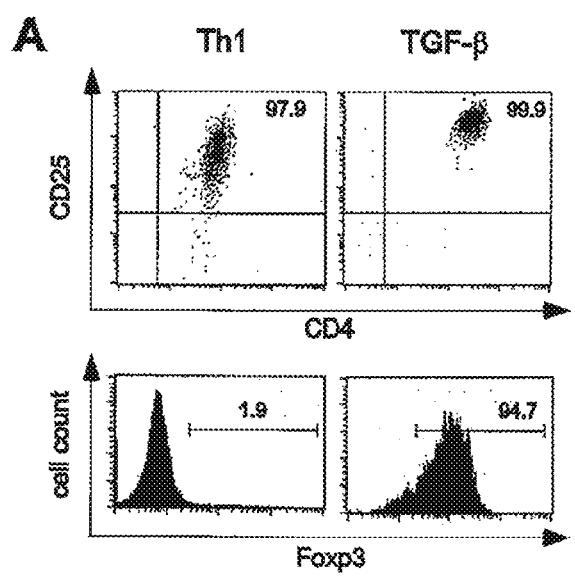 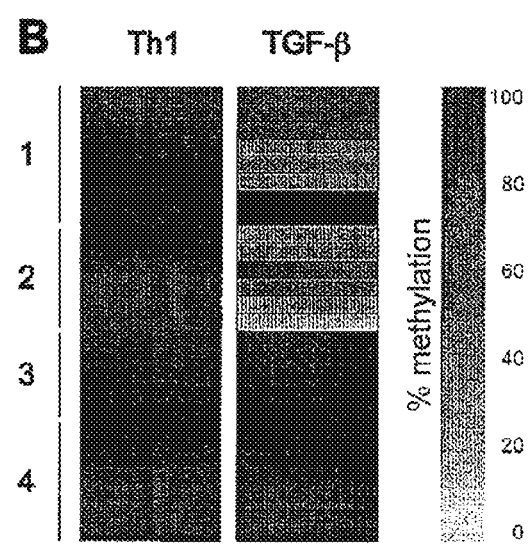
FIG. 2A                    FIG. 2B

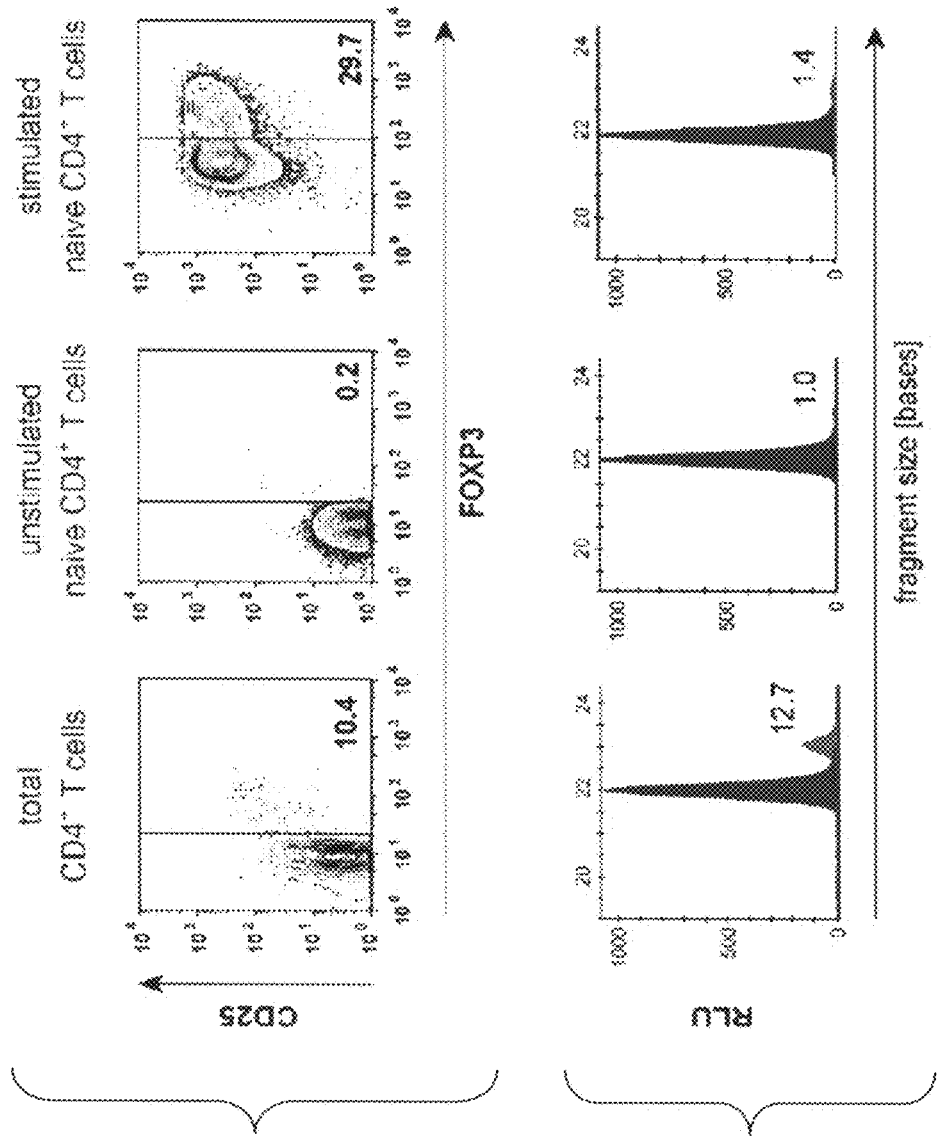

SEQUENCE LISTING

<160> NUMBER OF SEQ ID NOS: 31

<210> SEQ ID NO 1
<211> LENGTH: 22
<212> TYPE: DNA
<213> ORGANISM: Mus musculus

<400> SEQUENCE: 1
atttgaattg gatatggttt gt                                                22

<210> SEQ ID NO 2
<211> LENGTH: 22
<212> TYPE: DNA
<213> ORGANISM: Mus musculus

<400> SEQUENCE: 2
aaccttaaac ccctctaaca tc                                                22

<210> SEQ ID NO 3
<211> LENGTH: 21
<212> TYPE: DNA
<213> ORGANISM: Mus musculus

<400> SEQUENCE: 3
aggaagagaa gggggtagat a                                                 21

<210> SEQ ID NO 4
<211> LENGTH: 22
<212> TYPE: DNA
<213> ORGANISM: Mus musculus

<400> SEQUENCE: 4
aaactaacat tccaaaacca ac                                                22

<210> SEQ ID NO 5
<211> LENGTH: 22
<212> TYPE: DNA
<213> ORGANISM: Mus musculus

<400> SEQUENCE: 5
tggttgtttt ggagtttagt gt                                                22

<210> SEQ ID NO 6
<211> LENGTH: 22
<212> TYPE: DNA
<213> ORGANISM: Mus musculus

<400> SEQUENCE: 6
cacttttcta ccttccacaa at                                                22

<210> SEQ ID NO 7
<211> LENGTH: 22
<212> TYPE: DNA
<213> ORGANISM: Mus musculus

<400> SEQUENCE: 7
agaggttgaa ggaggagtat tt                                                22

<210> SEQ ID NO 8
<211> LENGTH: 22
<212> TYPE: DNA
<213> ORGANISM: Mus musculus

<400> SEQUENCE: 8
actatctatc caattcccca ac                                              22

<210> SEQ ID NO 9
<211> LENGTH: 22
<212> TYPE: DNA
<213> ORGANISM: Homo sapiens

<400> SEQUENCE: 9
gttatttgtg gagttttatg gg                                              22

<210> SEQ ID NO 10
<211> LENGTH: 22
<212> TYPE: DNA
<213> ORGANISM: Homo sapiens

<400> SEQUENCE: 10
ccccactact tacctctcta ca                                              22

<210> SEQ ID NO 11
<211> LENGTH: 21
<212> TYPE: DNA
<213> ORGANISM: Homo sapiens

<400> SEQUENCE: 11
aaaaccctcc tatctacctc c                                               21

<210> SEQ ID NO 12
<211> LENGTH: 22
<212> TYPE: DNA
<213> ORGANISM: Homo sapiens

<400> SEQUENCE: 12
agggtatgtg tttggttatt gt                                              22

<210> SEQ ID NO 13
<211> LENGTH: 22
<212> TYPE: DNA
<213> ORGANISM: Homo sapiens

<400> SEQUENCE: 13
aaacctcact tcttaatccc ta                                              22

<210> SEQ ID NO 14
<211> LENGTH: 22
<212> TYPE: DNA
<213> ORGANISM: Homo sapiens

<400> SEQUENCE: 14
ttgggatggt tttaagtgtt at                                              22

<210> SEQ ID NO 15
<211> LENGTH: 22
<212> TYPE: DNA
<213> ORGANISM: Homo sapiens

<400> SEQUENCE: 15
aaccctcaaa cctaactcat ac                                              22

<210> SEQ ID NO 16
<211> LENGTH: 22
<212> TYPE: DNA
<213> ORGANISM: Homo sapiens

<400> SEQUENCE: 16
ggaggtgata gtaaagaaag ga								22

<210> SEQ ID NO 17
<211> LENGTH: 20
<212> TYPE: DNA
<213> ORGANISM: Homo sapiens

<400> SEQUENCE: 17
tgtttggggg tagaggattt								20

<210> SEQ ID NO 18
<211> LENGTH: 20
<212> TYPE: DNA
<213> ORGANISM: Homo sapiens

<400> SEQUENCE: 18 tatcaccccca cctaaaccaa								20

<210> SEQ ID NO 19
<211> LENGTH: 22
<212> TYPE: DNA
<213> ORGANISM: Homo sapiens

<400> SEQUENCE: 19
aaatcctaaa atctcaaaac ca							22

<210> SEQ ID NO 20
<211> LENGTH: 21
<212> TYPE: DNA
<213> ORGANISM: Homo sapiens

<400> SEQUENCE: 20
ggtgatgatg gaggtatgtt a								21

<210> SEQ ID NO 21
<211> LENGTH: 21
<212> TYPE: DNA
<213> ORGANISM: Homo sapiens

<400> SEQUENCE: 21
tagagatggt aatagggga g								21

<210> SEQ ID NO 22
<211> LENGTH: 22
<212> TYPE: DNA
<213> ORGANISM: Homo sapiens

<400> SEQUENCE: 22
ccaacctcac aaaaactaaa ct							22

<210> SEQ ID NO 23
<211> LENGTH: 22
<212> TYPE: DNA
<213> ORGANISM: Homo sapiens

<400> SEQUENCE: 23
gtgaggttgg gttttatatt gt							22

<210> SEQ ID NO 24
<211> LENGTH: 22
<212> TYPE: DNA
<213> ORGANISM: Homo sapiens

```
<400> SEQUENCE: 24
tatccctatc tctcaaccaa tc                                              22

<210> SEQ ID NO 25
<211> LENGTH: 22
<212> TYPE: DNA
<213> ORGANISM: Homo sapiens

<400> SEQUENCE: 25
tcctaattca cacaccaaaa ta                                              22

<210> SEQ ID NO 26
<211> LENGTH: 23
<212> TYPE: DNA
<213> ORGANISM: Homo sapiens

<400> SEQUENCE: 26
aaggttaaaa ggagattaag agg                                             23

<210> SEQ ID NO 27
<211> LENGTH: 22
<212> TYPE: DNA
<213> ORGANISM: Homo sapiens

<400> SEQUENCE: 27
aattttacct aatccccaca tt                                              22

<210> SEQ ID NO 28
<211> LENGTH: 22
<212> TYPE: DNA
<213> ORGANISM: Homo sapiens

<400> SEQUENCE: 28
ggttgttggt ttagaaagtg tt                                              22

<210> SEQ ID NO 29
<211> LENGTH: 23
<212> TYPE: DNA
<213> ORGANISM: Homo sapiens

<400> SEQUENCE: 29
aggagtagga gattttattt tgg                                             23

<210> SEQ ID NO 30
<211> LENGTH: 22
<212> TYPE: DNA
<213> ORGANISM: Homo sapiens

<400> SEQUENCE: 30
ttcaactacc taacctcaac ct                                              22

<210> SEQ ID NO 31
<211> LENGTH: 23
<212> TYPE: DNA
<213> ORGANISM: Homo sapiens

<400> SEQUENCE: 31
cccaacaaac aatacaaaaa acc                                             23
```

DETECTION AND QUALITY CONTROL OF REGULATORY T CELLS THROUGH DNA-METHYLATION ANALYSIS OF THE FOXP3 GENE

CROSS-REFERENCE TO RELATED APPLICATION

This application claims the benefit of U.S. Provisional Application Ser. No. 60/777,631, filed Feb. 28, 2006, which is hereby incorporated by reference in its entirety, including including any figures, tables, nucleic acid sequences, and amino acid sequences.

BACKGROUND OF THE INVENTION

Regulatory T cells play an important role for the maintenance of immunological tolerance by suppressing the action of autoreactive effector cells, making them interesting targets for therapeutic applications. Therefore, these cells are critically involved in preventing the development of autoimmune reactions (Sakaguchi, Nat Immunol 6:345-352, 2005).

The transcription factor Foxp3 is specifically expressed in regulatory T cells and is thought to function as a master switch for the development and function of these cells. Recently, it has been demonstrated that ectopic expression of Foxp3 in conventional T cells confers suppressive activity (Fontenot and Rudensky, Nat Immunol 6:331-337, 2005).

The vast majority of Foxp3$^+$ regulatory T cells is generated during T cell development within the thymus, and it is thought that they represent an individual lineage. In addition, it also has been reported that Foxp3$^+$ regulatory T cells arise from conventional T cells both in vitro and in vivo upon antigen recognition under tolerogenic conditions. In all cases the expression of Foxp3 is characteristic for the development of regulatory T cells.

It is largely unknown, which signals lead to the expression of Foxp3, although some factors including TGF-β have been reported to induce Foxp3 expression in conventional T cells. However, it is unclear so far, whether these conditions only lead to a transient expression or to a terminal differentiation into Foxp3$^+$ regulatory T cells, which is required for long term suppressive function of these cells. Therefore, the starting point for the present invention was the analysis of mechanisms leading to stable expression of the transcription factor Foxp3 in regulatory T cells.

WO 02/090600 describes isolated nucleic acid molecules which encode Fkhsf, as well as mutant forms thereof. Also described are expression vectors suitable for expressing such nucleic acid molecules, and host cells containing such expression vectors. Also described are pharmaceutical compounds and methods of identifying such compounds that can modulate the immune system. In addition are provided methods for identifying proteins regulated by Scurfin and proteins that induce or inhibit Foxp3 expression.

Chen et al. (Chen L, Cohen A C, Lewis D B. Impaired Allogeneic Activation and T-helper 1 Differentiation of Human Cord Blood Naive CD4 T Cells. Biol Blood Marrow Transplant. 2006 February; 12(2): 160-71.) describe FoxP3 protein expression as a marker for regulatory CD25(high) CD4 T cells.

Even though almost all cells in an individual contain the exact same complement of DNA code, higher organisms must impose and maintain different patterns of gene expression in the various tissue types. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types.

The primary target of methylation is the two-nucleotide sequence Cytosine-Guanine (a 'CpG site'); within this context cytosine (C) can undergo a simple chemical modification to become 5-methyl-cytosine. In the human genome, the CG sequence is much rarer than expected except in certain relatively dense clusters called 'CpG islands'. CpG islands are frequently associated with gene promoters, and it has been estimated that more than half of the human genes have CpG islands (Antequera and Bird, Proc Natl Acad Sci USA. 90:11995-9, 1993).

Aberrant methylation of DNA frequently accompanies the transformation from healthy to cancerous cells. Among the observed effects are genome-wide hypomethylation, increased methylation of tumour suppressor genes and hypomethylation of many oncogenes (reviewed by Jones and Laird, Nature Genetics 21:163-167, 1999; Esteller, Oncogene 21:5427-5440, 2002; Laird, Nature Reviews/Cancer 3:253-266, 2003). Methylation profiles have been recognised to be tumour specific (i.e., changes in the methylation pattern of particular genes or even individual CpGs are diagnostic of particular tumour types) and there is now an extensive collection of diagnostic markers for bladder, breast, colon, oesophagus, stomach, liver, lung, and prostate cancers (summarised by Laird, Nature Reviews/Cancer 3:253-266, 2003).

Epigenetic control by methylation is essential for early development including embryogenesis, X-chromosome inactivation and imprinting (monoallelic silencing) of either the paternal or maternal allele (Erlich, J Cellular Chem 88:899-910, 2003). There is also a class of genes that is active in the germ line, but is silenced by methylation in somatic cells (Bird, Genes and Dev 16:6-21, 2002; Li, Nature Reviews/Genetics 3:662-673, 2002).

Tissue-specific methylation also serves in regulating adult cell types/stages, and in some cases a causal relationship between methylation and gene expression has been established. The following is a partial list of genes, for which methylation changes are strongly implicated in controlling gene expression in tissue-specific manner: Lactate dehydrogenase C (testes); Oxytocin receptor (blood & liver); Tyrosine aminotransferase (liver); GFAP (astrocytes); and Leukosialin (leukocytes). In other cases, methylation may be a by-product of some other primary regulation, or it is required to lock the gene in the "off" state (Erlich, J Cellular Chem 88:899-910, 2003). For the present applications (cell/tissue identification), a causal relationship is not required, merely a strong correlation between methylation patterns and cell types.

A previously published example for such a cell type and cell status specific modification of certain gene regions is found during the lineage commitment of T cells to helper T cells (Th1 or Th2). Naïve (unstimulated) CD4$^+$ T cells become activated upon encountering an antigen and can be committed to alternative cell fates through further stimulation by interleukins. The two types of helper T cells show reciprocal patterns of gene expression; Th1 produces Interferon-gamma (IFN-γ) and silences IL-4, while Th2 produces IL-4 and silences IFN-γ (Ansel et al., Nature Immunol 4:616-623, 2003). For both alternative cell fates, the expression of these genes is inversely correlated with methylation of proximal CpG sites. In Th2 and naïve T cells the IFN-γ promoter is methylated, but not in Th1 cells where IFN-γ is expressed (Attwood et al., CMLS 59:241-257, 2002). Conversely, the entire transcribed region of IL-4 becomes demethylated under Th2-inducing conditions, which strongly correlates with efficient transcription of IL-4. In Th1 cells, this extensive demethylation does not occur, rather particular untranscribed regions gradually become heavily methylated and IL-4 is not expressed (Lee et al., Immunity 16:649-660, 2002). Furthermore, Bruniquel and Schwartz (Nat Immunol. 4:235-40, 2003) have demonstrated that in naïve T cells, the IL-2 promoter is heavily methylated and inactive, but after activation of the naïve T cell, the IL-2 gene undergoes rapid and specific demethylation at six consecutive CpGs. This alteration in methylation patterns occurs concomitantly with cell differentiation and increased production of the IL-2 product.

It is an object of the present invention, to provide an improved method of expression analysis and in particular expression analysis based on DNA methylation analysis as a superior tool that can supplement or replace conventional methodologies as an indicator of cell type and status in vertebrates, in order to reliably identify FoxP3-positive regulatory T cells, preferably $CD25^+CD4^+$ regulatory T cells, of a mammal and/or in a mammal.

BRIEF SUMMARY OF THE INVENTION

The present invention relates to a method, in particular an in vitro method, for identifying FoxP3 positive (preferably $CD25^+CD4^+$) regulatory T cells of a mammal, comprising analysing the methylation status of at least one CpG position in the gene foxp3 or an orthologous or paralogous gene thereof, and the use of DNA-methylation analysis of the gene of the transcription factor FoxP3 for a detection and quality assurance and control of regulatory T cells. Furthermore, the present invention relates to a kit for performing the above methods as well as respective uses.

For the purpose of the present invention all references as cited herein as well as the sequence listing are incorporated by reference in their entireties.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 2A and 2B shows cells stimulated in the presence of TGF-β that are Foxp3+. In (FIG. 2B), a demethylation can be observed.

FIG. 5A) MACS sorted CD4+ T cells isolated from peripheral blood were stained for CD25 and CD45RA and sorted into $CD25^{high}$CD45RA−Tregs and CD25-CD45RA+ naïve T cells by FACS. Flow cytometry analysis shows staining of cells before FACS sorting (left panel) as well as the sort purity and FOXP3 expression in sorted CD25-CD45RA+ naïve T cells and $CD25^{high}$CD45RATregs (middle and right panels, respectively). Numbers display frequency of cells within indicated populations. Stainings of cells from one representative donor are depicted. FIG. 5B) Schematic overview of the FOXP3 gene and positioning of amplicons designed for methylation analysis (upper panel). The lower panel depicts merged CpG methylation rates measured by bisulfite sequencing from donors #1-3; each box represents methylation rate of a single CpG according to the color code (yellow=0% methylation, blue=100% methylation).

FIGS. 7A and 7B shows that the conserved region of FOXP3 gene is fully methylated in activated conventional CD4+ T cells. CD4+ T cells from male donor #17 were sorted into naïve CD25-CD45RA+CD4+ T cells by FACS and stimulated in vitro for 4 days. FIG. 7A) Flow cytometry analysis shows staining of MACS-sorted total CD4+ T cells (left panel), FACS-sorted naïve CD25-CD45RA+CD4+ T cells (middle panel) and stimulated nave CD4+ T cells for CD25 and FOXP3. Numbers indicate frequency of FOXP3+ cells among total CD4+ T cells and FACS-sorted nave CD4+ T cells (left and middle panel, respectively) as well as FOXP3high cells among stimulated naïve CD4+ T cells (right panel). FIG. 7B) MS-SNuPE analysis of a single CpG motif within Amp5 in total CD4+ T cells (left panel), FACS-sorted naïve CD25-CD45RA+CD4+ T cells (middle panel) and stimulated naïve CD4+ T cells. Blue peaks correspond to a methylated cytosine and green peaks correspond to unmethylated cytosine. Original data are shown in the electropherogram (X-axis: fragment size in bases; Y-axis: signal intensities in relative light units). Numbers display frequency of unmethylated cytosines.

BRIEF DESCRIPTION OF SEQUENCES

SEQ ID NOs: 1 to 8 show primers as used for the particular amplicons 1 to 4 as described in the examples with respect to murine data.

SEQ IDs NOs: 9 to 31 show primers as used for the particular amplicons 1 to 11 and the MS-SNuPE as described in the examples with respect to human data.

DETAILED DISCLOSURE OF THE INVENTION

According to a first aspect thereof, the present invention solves the above object by providing a method for identifying FoxP3-positive regulatory T cells, preferably $CD25^+$ $CD4^+$ regulatory T cells of a mammal, comprising analysing the methylation status of at least one CpG position in the gene foxp3 or an orthologous or paralogous gene thereof.

Said method can be performed in vitro and/or in vivo. Preferred is a method according to the invention, wherein said FoxP3-positive regulatory T cells, preferably CD25+ CD4+ regulatory T cells are stable FoxP3-positive regulatory T cells, preferably stable CD25+CD4+ regulatory T cells. The analysis of the accessibility of the Foxp3 locus provides additional information, besides the mere expression of Foxp3, to what extent a permanent conversion into a regulatory T cell lineage has occurred (see also below in the context of TGF-β—induced regulatory T cells).

More preferably, said analysis of the methylation status according to the invention comprises analysing the methylation status of at least one CpG position in the 5' region upstream from the transcription start, promoter regions, introns, and/or exon/intron borders of the gene foxp3.

The inventors have identified a particular region within the Foxp3 gene, which are functionally involved in the regulation of stable Foxp3 expression in regulatory T cells. This region contains many CpG motifs, which display a differential methylation status when cells expressing Foxp3 (preferably CD25+CD4+) compared with cells not expressing Foxp3 (preferably CD25−CD4+), if, for example, the bisulphite sequencing method is used. The inventors could demonstrate that in Foxp3+ cells the CpG motifs are almost completely demethylated (i.e. to more than 70%, preferably 80%, preferably, more than 90% and most preferred more than 95%), whereas the same motifs are completely methylated in Foxp3− cells. The differential methylation of the CpG motifs within the aforementioned region strongly correlates with Foxp3 expression. Thus, determination of the methylation status of the foxp3 locus could become a valuable tool to identify stable populations of regulatory T cells required for clinical application in the treatment of autoimmune disease, transplant rejection or allergy.

Figure 1:
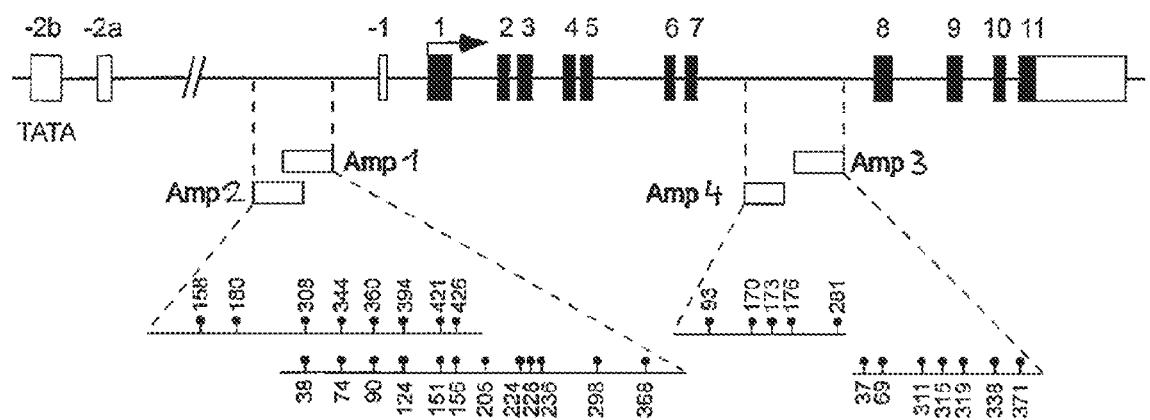
FIG. 1 shows the schematic structure of the foxp3 murine locus with introns, exons and regulatory sequences. Furthermore, the amplicons are indicated, together with CpG positions as shown in FIG. 3.

The lymphoproliferative disorder of scurfy mice is completely rescued by transgenic complementation with a 30.8-kb genomic fragment containing the Foxp3 gene from wild type mice (Brunkow M E, Jeffery E W, Hjerrild K A, Paeper B, Clark L B, Yasayko S A, Wilkinson J E, Galas D, Ziegler S F, Ramsdell F. Disruption of a new forkhead/winged-helix protein, scurfin, results in the fatal lymphoproliferative disorder of the scurfy mouse. Nat Genet. 2001 January; 27(1):68-73.). This indicates that all regulatory elements required for proper Foxp3 expression are located within the transgene including the entire gene as well as 12.5 kb and 2.8 kb of 5' and 3' flanking sequences, respectively. The inventors therefore focused the analysis of epigenetic modifications on sequences from the 30.8-kb region and selected specific regions for methylation analysis based on CpG density. Upon electronic PCR, primers were designed to produce four amplicons (see FIG. 1): Overlapping amplicons 1 and 2 map upstream from exon-1, amplicon 3 and 4 align to the 7th intron. No CpG-rich regions were observed within the predicted Foxp3 promoter located at the putative 5' end of exon −2b, 6.1 kb upstream from the first coding exon (Brunkow M E, Jeffery E W, Hjerrild K A, Paeper B, Clark L B, Yasayko S A, Wilkinson J E, Galas D, Ziegler S F, Ramsdell F. Disruption of a new forkhead/winged-helix protein, scurfin, results in the fatal lymphoproliferative disorder of the scurfy mouse. Nat Genet. 2001 January; 27(1):68-73.).

Figure 4:
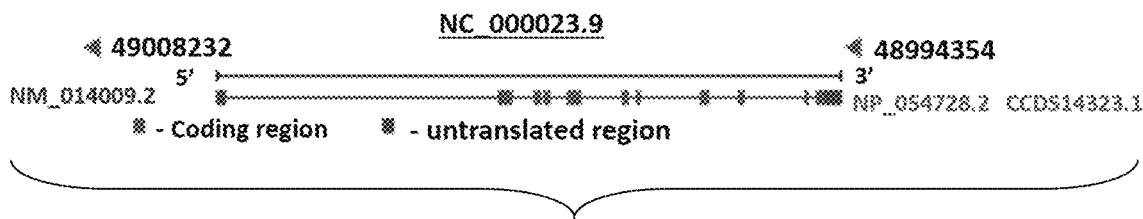
FIG. 4 shows the genetic organisation of the human foxp3 gene in Accession Number NC_000023.
Figure 5A:
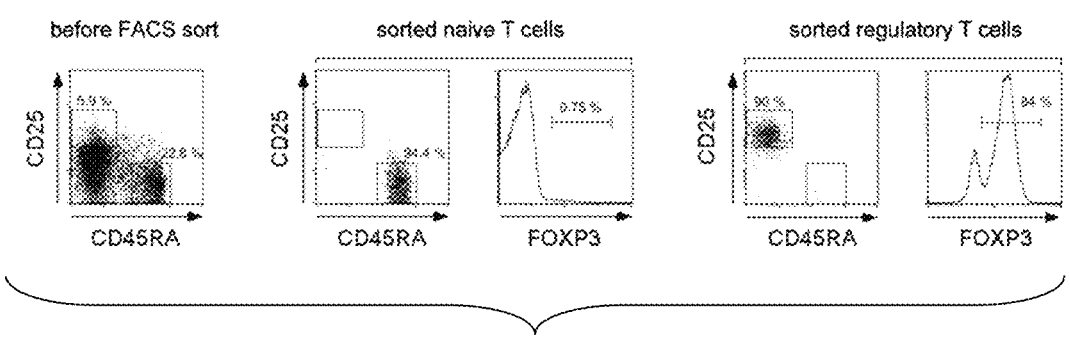
FIGS. 5A and 5B show demethylation of the FOXP3 gene in Foxp3+$CD25^{high}$CD4+ Tregs.

In the context of the present invention, the term "gene" shall mean a region of the chromosomal DNA that encodes for a certain protein, such as FoxP3, and contains other genetic elements that are responsible for the regulation of said gene. Thus, a gene includes also introns, enhancers, promoter sequences and the 5' untranslated region of the gene. In the present case, the gene will not only include the sequence as given in Brunkow et al. (Brunkow M E, Jeffery E W, Hjerrild K A, Paeper B, Clark L B, Yasayko S A, Wilkinson J E, Galas D, Ziegler S F, Ramsdell F. Disruption of a new forkhead/winged-helix protein, scurfin, results in the fatal lymphoproliferative disorder of the scurfy mouse. Nat Genet. 2001 January; 27(1):68-73. Accession number AF277993), but also includes the untranslated regions upstream and downstream thereof, as depicted in FIG. 4 as available in the database under Accession number NC_000023, and FIG. 4 5.

Initially, all analyses as performed for the present invention have been performed in the murine system. Nevertheless, the region that shows differential methylation of CpG motifs between Foxp3+ and Foxp3− cells, is highly conserved between mammals, in particular between mice and human. In addition, first experiments showed that in the human system the same and/or homologous CpG motifs are demethylated as in murine foxp3+ regulatory T cells. In the context of the present invention, this fact is described by the terms "orthologous" or "paralogous" gene. An "ortholog" is a gene in two or more species that has evolved from a common ancestor, and is also called an orthologous gene. In the context of the present invention, *Homo sapiens* FoxP3 (forkhead box P3) is therefore an ortholog of the Mus musculus Foxp3 (forkhead box P3) gene and/or protein. Other orthologs are *C. familiaris* LOC491876 (similar to Forkhead box protein P3), and R. norvegicus LOC317382 (similar to scurfin). "Paralogs" are genes related by duplication within a genome and are also called a paralogous gene. Orthologs retain the same function in the course of evolution, whereas paralogs evolve new functions, even if these are related to the original one. Included in the term "paralog" is a "pseudogene" that is a nucleotide sequences that is similar to a normal gene, but does not produce a functional final product. There are two variants of pseudogenes. The first requires the final product to be a protein. The second allows the final product to be an RNA.

Based on the information as given herein, the person of skill will be readily able, to compare the orthologous or paralogous genes (for example using a computer program in order to align the sequences, such as the fasta program), and to identify regions and/or CpG positions that can be found in the same regions and/or even at the same equivalent positions in the (both) genes. According to the present invention, these regions and/or CpG positions are regarded as orthologous or paralogous. Usually, an alignment is based on the level of sequence identity between the two (or more) DNA fragments that are analyzed. As a preferred example according to the present invention, a 384-bp stretch that is differentially methylated in the region as covered by amplicons 1 and 2 (as described herein), but not the region covered by amplicons 3 and 4 is highly conserved between mice and men (80.7% sequence identity), suggesting that in both mammals functionally important parts can be found that are both subject to epigenetic regulation. As another preferred example according to the present invention, the Treg-specific demethylated region (TSDR) could be identified. Other levels of sequence identity are preferably about 75%, more preferably about 80%, and most preferred about 90% of a given fragment.

In a preferred embodiment of the method according to the present invention, said analysis of the methylation status comprises amplification with at least one of the primer pairs selected from SEQ ID NO: 1 and 2; SEQ ID NO: 3 and 4; SEQ ID NO: 5 and 6; SEQ ID NO: 7 and 8, SEQ ID NO: 9 and 10; SEQ ID NO: 11 and 12; SEQ ID NO: 13 and 14;

SEQ ID NO: 15 and 16; SEQ ID NO: 17 and 18; SEQ ID NO: 19 and 20; SEQ ID NO: 21 and 22; SEQ ID NO: 23 and 24; SEQ ID NO: 25 and 26; SEQ ID NO: 27 and 28; SEQ ID NO: 29 and 30, and orthologous or paralogous primer pairs thereof. Preferably, the amplification involves a polymerase enzyme, a PCR or chemical amplification reaction, or other amplification methods as known to the person of skill as described below, e.g. in the context of MSP, HeavyMethyl, or MethyLight. With the amplification, amplicons 1 to 4 or human amplicans 1 to 11 (as described herein) or orthologs or paralogs thereof are produced that are particularly preferred "tools" for performing the method(s) according to the present invention. Consequently, an oligomer according to any of SEQ ID NO: 1 to 30 or an amplicon as amplified by a primer pair selected from SEQ ID NO: 1 and 2; SEQ ID NO: 3 and 4; SEQ ID NO: 5 and 6; SEQ ID NO: 7 and 8, SEQ ID NO: 9 and 10; SEQ ID NO: 11 and 12; SEQ ID NO: 13 and 14; SEQ ID NO: 15 and 16; SEQ ID NO: 17 and 18; SEQ ID NO: 19 and 20; SEQ ID NO: 21 and 22; SEQ ID NO: 23 and 24; SEQ ID NO: 25 and 26; SEQ ID NO: 27 and 28; SEQ ID NO: 29 and 30, or and orthologous or paralogous oligomers or amplicons constitute preferred embodiments of the present invention. Particularly preferred is the primer pair SEQ ID NO: 17 and 18 and human amplicon 5 ("Amp5").

Based on the above information and the data as obtained from the murine system, orthologous or paralogous primer pairs can be designed by the person of skill having a sequence identity with the above primers of preferably about 75%, more preferably about 80%, and most preferred about 90%. Particularly preferred is a method according to the present invention, wherein said analysis of the methylation status comprises amplification with at least one of the primer pairs selected from SEQ ID NO: 1 and 2; SEQ ID NO: 3 and 4; SEQ ID NO: 15 and 16; SEQ ID NO: 17 and 18, SEQ ID NO: 19 and 20; SEQ ID NO: 21 and 22; SEQ ID NO: 23 and 24; SEQ ID NO: 29 and 30; and orthologous or paralogous primer pairs thereof.

Further preferred is a method according to the present invention, wherein the analysis of the methylation status comprises analysing the methylation status of at least one CpG position selected from the group consisting of nucleotide positions 38, 74, 90, 124, 151, 156, 205, 224, 228, 236, 298, and 368 of the amplicon 2 as amplified by the primer pair SEQ ID NO: 1 and 2, nucleotide positions 158, 180, 308, 344, 360, 394, 421, and 426 of the amplicon 1 as amplified by the primer pair SEQ ID NO: 3 and 4, nucleotide positions 37, 69, 311, 315, 319, 338, and 371 of the amplicon 4 as amplified by the primer pair SEQ ID NO: 5 and 6, nucleotide positions 93, 170, 173, 176, and 281 of the amplicon 3 as amplified by the primer pair SEQ ID NO: 7 and 8, and orthologous or paralogous CpG positions thereof.

Even more preferred is a method according to the present invention, wherein said analysis of the methylation status comprises analysing the methylation status of at least one CpG position selected from the group consisting of positions 38, 74, 90, 124, 156, 205, 224, 236, 298, and 368 of the amplicon 2 as amplified by the primer pair SEQ ID NO: 1 and 2, positions 180, 308, 344, and 394 of the amplicon 1 as amplified by the primer pair SEQ ID NO: 3 and 4, and orthologous or paralogous CpG positions thereof. It could be shown in the experiments that these positions were mostly demethylated in the regulatory T cells. The person of skill will furthermore be able to select specific subsets of CpG positions in order to minimise the amount of sites to be analyzed, for example all sites as present on amplicon 1 or all sites as present on amplicon 2 or orthologous or paralogous CpG positions thereof.

In order to analyze the methylation status of CpG positions, any known method to analyse DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

The method according to the present invention can be performed with any mammal having the foxp3 gene or an ortholog or paralog thereof, preferred is a method according to the present invention, wherein said mammal is a mouse, rat, monkey or human.

In another aspect of the present invention, the method according to the present invention further comprises an induction with TGF-β. A critical issue for application of regulatory T cells in therapeutical approaches is the availability of large numbers of cells. Recent publications have reported that conventional $CD25^-CD4^+$ T cells can be converted into $Foxp3^+$ regulatory T cells by stimulation in presence of TGF-β (Chen W, Jin W, Hardegen N, Lei K J, Li L, Marinos N, McGrady G, Wahl S M. Conversion of peripheral $CD4^+CD25^-$ naive T cells to $CD4^+CD25^+$ regulatory T cells by TGF-beta induction of transcription factor Foxp3. J Exp Med. 15 Dec. 2003; 198(12):1875-86.), (Park H B, Paik D J, Jang E, Hong S, Youn J. Acquisition of anergic and suppressive activities in transforming growth factor-beta-costimulated $CD4^+CD25^-$ T cells. Int Immunol. 2004 August; 16(8):1203-13. Epub 2004 Jul. 5), (Fu S, Zhang N, Yopp A C, Chen D, Mao M, Chen D, Zhang H, Ding Y, Bromberg J S. TGF-beta induces Foxp3+T-regulatory cells from CD4+CD25–precursors. Am J Transplant. 2004 October; 4(10):1614-27.), (Fantini M C, Becker C, Monteleone G, Pallone F, Galle P R, Neurath M F. Cutting edge: TGF-beta induces a regulatory phenotype in CD4+CD25– T cells through Foxp3 induction and down-regulation of Smad7. J Immunol. 1 May 2004; 172(9):5149-53.), (Wan Y Y, Flavell R A. Identifying Foxp3-expressing suppressor T cells with a bicistronic reporter. Proc Natl Acad Sci USA. 5 Apr. 2005; 102(14):5126-31. Epub 28 Mar. 2005.), (Fantini M C, Becker C, Tubbe I, Nikolaev A, Lehr H A, Galle P R, Neurath M F. TGF-(beta) induced Foxp3+ regulatory T cells suppress Th1-mediated experimental colitis. Gut. 14 Sep. 2005). However, stability and in vivo efficacy of these cells have not been thoroughly tested so far. Analysis of the accessibility of the Foxp3 locus might provide an additional hint, beside the mere expression of Foxp3, to what extent a permanent conversion into a regulatory T cell lineage did occur. The inventors therefore analyzed the methylation status of the Foxp3 locus from $CD25^-CD4^+$ T cells, which had been activated and cultured for 5 days in the presence of TGF-β. On day 5, control cells cultured under Th1 conditions showed minor Foxp3-expression (<2%), whereas almost 95% of the cells stimulated in the presence of TGF-β were $Foxp3^+$ with partial demethylation (FIG. 2A). Interestingly, a partial demethylation was only observed in the cells stimulated in the presence of TGF-β.

In another aspect of the present invention, the present invention provides a method for diagnosing the immune status of a mammal, comprising the steps of a) obtaining a sample containing T-cells from said mammal to be diagnosed, b) analysing the methylation status of at least one CpG position in the gene foxp3 or an orthologous or paralogous gene thereof according to the present invention in said T-cells, c) identifying the amount of regulatory T-cells present in said sample based on said methylation status, and d) concluding on the immune status of said mammal based on said amount as identified. In one aspect of this particular method, the total population of T cells in a sample (containing regulatory and non-regulatory T-cells) is analyzed for their methylation status in the foxp3 gene. Based on the result of the overall methylation frequency of the sites, the ratio and/or amount of regulatory T cells inside the analyzed population can be determined. From said result, it can be concluded on the immune status and/or T cell status of the mammal as diagnosed. The method can be performed in vitro and/or in vivo. In general, all biological samples can be used, as long as they contain suitable T-cells. Preferred is a method, wherein said sample is selected from a blood sample, a sample of blood lymphocytes or a fraction thereof.

The method according to the present invention can be performed with any mammal having the foxp3 gene or an ortholog or paralog thereof, preferred is a method according to the present invention, wherein said mammal is a mouse, rat, monkey or human. Preferred is a method, wherein said mammal is a patient suffering from a disease selected from autoimmune diseases, adverse effects in allotransplantate recipients, tumorous diseases, ovarian cancer, chronic graft-versus-host disease, allergic asthma, multiple sclerosis, and IPEX syndrome. These diseases have already been described herein.

Further preferred is a method, wherein the amount of regulatory T-cells corresponds to a demethylation of the CpG positions as analyzed to at least 80%, preferably 90%, and more preferably 95%. Even further preferred is a method that is further comprising measuring and/or monitoring the amount or ratio of said regulatory T cells in response to chemical and/or biological substances that modulate foxp3 expression in the regulatory T cell. That is, changes in the amount or ratio of regulatory T cells that are caused by, for example, the treatment of a disease (e.g. as described herein), and the success and/or progress of said treatment in terms of an effect on regulatory T cells can be followed using this method. A follow-up of the methylation pattern of T cells based on the marker herein will point to changes in the cells that are due to a response to said chemical and/or biological substances, in some cases even before a phenotypic change can be observed.

In yet another aspect of the present invention, the present invention provides a method for determining the suitability of in vitro generated or expanded regulatory T cells for a transfer into a patient, comprising the method according to the present invention, and detecting, whether the CpG positions as analyzed are demethylated to at least 80%, preferably 90%, and more preferably 95%. The method can be performed in vitro and/or in vivo. For example, T cells that appear to show a modified, in particular a drop, of foxp3 expression are usually not regarded as stable and will not be used further.

In yet another aspect of the present invention, the present invention provides a method for identifying chemical and/or biological substances that modulate foxp3 expression in a T cell, comprising contacting one or more of said chemical and/or biological substance with a T cell, performing the method according to the present invention as described above, and detecting, whether said chemical and/or biological substance modulates methylation of the CpG positions as analyzed. The method can be performed in vitro and/or in vivo. In this aspect, the present invention encompasses a method, sometimes called a "screening-method", that seeks to identify chemical and/or biological substances modulating foxp3 expression that can be used as starting points for the development of regulatory T cell specific medication and respective pharmaceutical compositions. The present method is based on the fact that it is well accepted that the foxp3 gene plays a central role for the development of regulatory T cells. Therefore, factors modulating Foxp3 expression are also interesting tools to treat autoimmune diseases or allotransplantate recipients. Even factors preventing Foxp3 expression are interesting for the treatment of tumour patients, where Foxp3$^+$ regulatory T cells have been shown to prevent a strong anti tumour response. Such factors, which lead to a stable modification of Foxp3 expression, can be detected with the method described in this invention. Furthermore, factors that can enhance the differentiation of regulatory T-cells and lead to an alleviation of autoimmune and allergenic disorders can be identified with the present method. Chemical and/or biological substances that are suitable as screening compounds are known to the person of skill and, for example, include small molecules, peptides and proteins, and antibodies or fragments thereof. Furthermore, the screening can be done using a commercially compound library, optimally together with suitable automation, such as a robot. In one preferred embodiment of the method for identifying chemical and/or biological substances, said substance provides a demethylation of the CpG positions as analyzed to at least 80%, preferably 90%, and more preferably 95%.

The expression of FoxP3 is described as being associated with poor prognosis in ovarian cancer (Wolf, D., et al. The expression of the regulatory T cell-specific forkhead box transcription factor FoxP3 is associated with poor prognosis in ovarian cancer. Clin. Cancer Res. 11 (23), 8326-8331 (2005)). High expression levels of FoxP3 are associated with ovarian cancer. Furthermore, the gene expression of regulatory T cells transcription factor FOXP3 was reduced in chronic graft-versus-host disease patients (Zorn, E., et al. Reduced frequency of FOXP3+ CD4+CD25+ regulatory T cells in patients with chronic graft-versus-host disease. Blood 106 (8), 2903-2911 (2005)) In addition, a role of FoxP3 in allergic asthma has been described (Schmidt-Weber, C. B. and Blaser, K. The role of the FOXP3 transcription factor in the immune regulation of allergic asthma. Curr Allergy Asthma Rep 5 (5), 356-361 (2005)). The IPEX syndrome is characterized by the development of overwhelming systemic autoimmunity in the first year of life resulting in the commonly observed triad of watery diarrhea, eczematous dermatitis, and endocrinopathy seen most commonly as insulin-dependent diabetes mellitus. Most individuals have other autoimmune phenomena including Coombs positive anemia, autoimmune thrombocytopenia, autoimmune neutropenia, and tubular nephropathy The majority of affected males die within the first year of life of either metabolic derangements or sepsis; a few have survived into the second and third decade. Until now, the diagnosis of is based on clinical findings, and foxp3 is the only gene currently known to be associated with IPEX syndrome. Approximately 60% of males with IPEX syndrome have mutations identified in the foxp3 gene. Recently, the expression of foxp3 was furthermore linked to autoimmune diseases such as multiple sclerosis (MS) (Huan J, Culbertson N, Spencer L, Bartholomew R, Burrows G G, Chou Y K, Bourdette D, Ziegler S F, Offner H, Vandenbark A A. Decreased FOXP3 levels in multiple sclerosis patients. J Neurosci Res. 1 Jul. 2005; 81(1):45-52.).

The above references clearly establish a connection between foxp3 expression and autoimmune diseases, adverse effects in allotransplantate recipients, tumorous diseases, ovarian cancer, chronic graft-versus-host disease, allergic asthma, and IPEX syndrome. Thus, another preferred method according to the present invention is a method for the diagnosis of diseases that are associated with the aberrant expression of the gene foxp3, comprising the method according to the present invention, and detecting, whether the CpG positions as analyzed are demethylated to at least 80%, preferably 90%, and more preferably 95%, wherein the diseases are selected from autoimmune diseases, adverse effects in allotransplantate recipients, tumorous diseases, ovarian cancer, chronic graft-versus-host disease, allergic asthma, and IPEX syndrome. The present method can be performed in vitro and/or in vivo, and allows for a more specific determination of the parameter FoxP3, as temporary expression of FoxP3, especially in the human system, has been detected also in activated, non-regulatory T cells (Ziegler S F. FOXP3: Of Mice and Men. Annu Rev Immunol. 1 Dec. 2005).

Another preferred aspect of the present invention relates to a kit for identifying regulatory T cells based on the analysis of the methylation status of CpG positions in the gene foxp3, comprising materials for performing a method according to the present invention. In one preferred embodiment according to the present invention, the kit comprises a) a bisulfite reagent, and b) materials for the methylation analysis of CpG positions selected from the positions consisting of positions 38, 74, 90, 124, 156, 205, 224, 236, 298, and 368 of the amplicon 2 as amplified by the primer pair SEQ ID NO: 1 and 2, positions 180, 308, 344, and 394 of the amplicon 1 as amplified by the primer pair SEQ ID NO: 3 and 4, positions in amplicon 5 as amplified by the primer pair SEQ ID NO: 17 and 18, and orthologous or paralogous CpG positions thereof. The person of skill will furthermore be able to select materials for specific subsets of CpG positions in order to minimise the amount of sites to be analyzed, for example all sites as present on amplicon 1 or all sites as present on amplicon 2 or all sites as present on amplicon 5 or orthologous or paralogous CpG positions thereof. The kit can be a diagnostic kit.

The kits according to the present invention may also contain: 1. Chemicals (bisulfite, etc.) for processing the cell samples; 2. Procedure protocols; 3. Oligonucleotide probes, amplicons, blockers or extension primers according to the present invention that will detect markers relevant to a particular cell type. The oligonucleotides would be constructed to generate a signal on a commonly available detection platform, such as Real Time-PCR (RT-PCR) or Single Base Extension (SBE). Each signal indicates the level of methylation at a particular target site in the sample. As an alternative, probes according to the described nucleic acids could be produced for usage on a chip; 4. A bioinformatic tool to process the results. This, e.g., software might normalise the signals from the raw data, contain a result matrix for interpretation of the read-out, or implement various algorithms that calculate, for example, cell type proportions, or potency predictions.

Yet another preferred aspect of the present invention relates to the use of an oligomer or amplicon according to the present invention or a kit according to the present invention for detecting and/or identifying FoxP3-positive regulatory T cells, preferably CD25$^+$CD4$^+$ regulatory T cells, in analogy to what has been described above.

Yet another preferred aspect of the present invention relates to a method of treatment of diseases that are related to Foxp3 expression, such as autoimmune diseases, adverse effects in allotransplantate recipients, tumorous diseases, ovarian cancer, chronic graft-versus-host disease, allergic asthma, multiple sclerosis, and IPEX syndrome. The method comprises administering an effective amount of stable FoxP3-positive regulatory T cells, preferably CD25$^+$CD4$^+$ regulatory T cells to said patient in need thereof. How to administer effective amount of stable FoxP3-positive regulatory T cells, preferably stable CD25$^+$CD4$^+$ regulatory T cells is described in the literature (for example in Bharat A, Fields R C, Mohanakumar T. Regulatory T cell-mediated transplantation tolerance. Immunol Res. 2006; 33(3):195-212. June C H, Blazar B R. Clinical application of expanded CD4(+)25(+) cells. Semin Immunol. 31 Jan. 2006; Khazaie K, von Boehmer H. The impact of CD4(+)CD25(+) Treg on tumor specific CD8(+) T cell cytotoxicity and cancer. Semin Cancer Biol. 2006 April; 16(2):124-136. Epub 26 Jan 2006, and the references as cited therein), and the person of skill will be able to apply these methods in the context of the present invention. The term "treatment" also includes a prevention of said Foxp3 expression related diseases.

The analysis of the methylation status of the region within the foxp3 locus allows an improved prediction whether the cell population will stably express the FoxP3 gene or not. Therefore, this method can be used as a quality control for in vitro generated or expanded regulatory T cells before adoptive transfer into patients which suffer from autoimmune diseases or which have received an allotransplant. Only if the CpG motifs are demethylated to a certain degree it is confident that these cells will stably express the Foxp3 gene and will not loose foxp3 expression after some period of time. This scenario would have a fatal outcome since the adoptively transferred cells could convert from Foxp3$^+$ regulatory T cells into pathogenic effector cells, which might lead to a worsening of the disease state. Therefore, a quality control concerning the stability of the regulatory phenotype of adoptively transferred cells is absolutely required and can be achieved by the analysis of the methylation status of the aforementioned region of the Foxp3 locus.

In human, almost complete demethylation was found in natural FOXP3+CD25$^{high}$CD4+ Tregs for several regions in the FOXP3 gene. In contrast, most regions were methylated in naïve CD45RA+CD25−CD4+ T cells. Activated conventional CD4+ T cells, expressing FOXP3 transiently, displayed no FOXP3 DNA demethylation, indicating that DNA modification only occurs during development of stable FOXP3+CD25$^{high}$CD4+ Tregs. The inventors conclude that FOXP3 DNA demethylation is rather linked to Treg function than to FOXP3 protein expression. Accordingly, determination of the methylation status of the conserved region offers a reliable criterion for Treg identification and quantification.

Since demethylation of the FOXP3 gene is only associated with Tregs constitutively expressing FOXP3, allowing a better surrogate for determining the "true" regulatory phenotype than analyzing FOXP3 protein expression.

Figure 3:
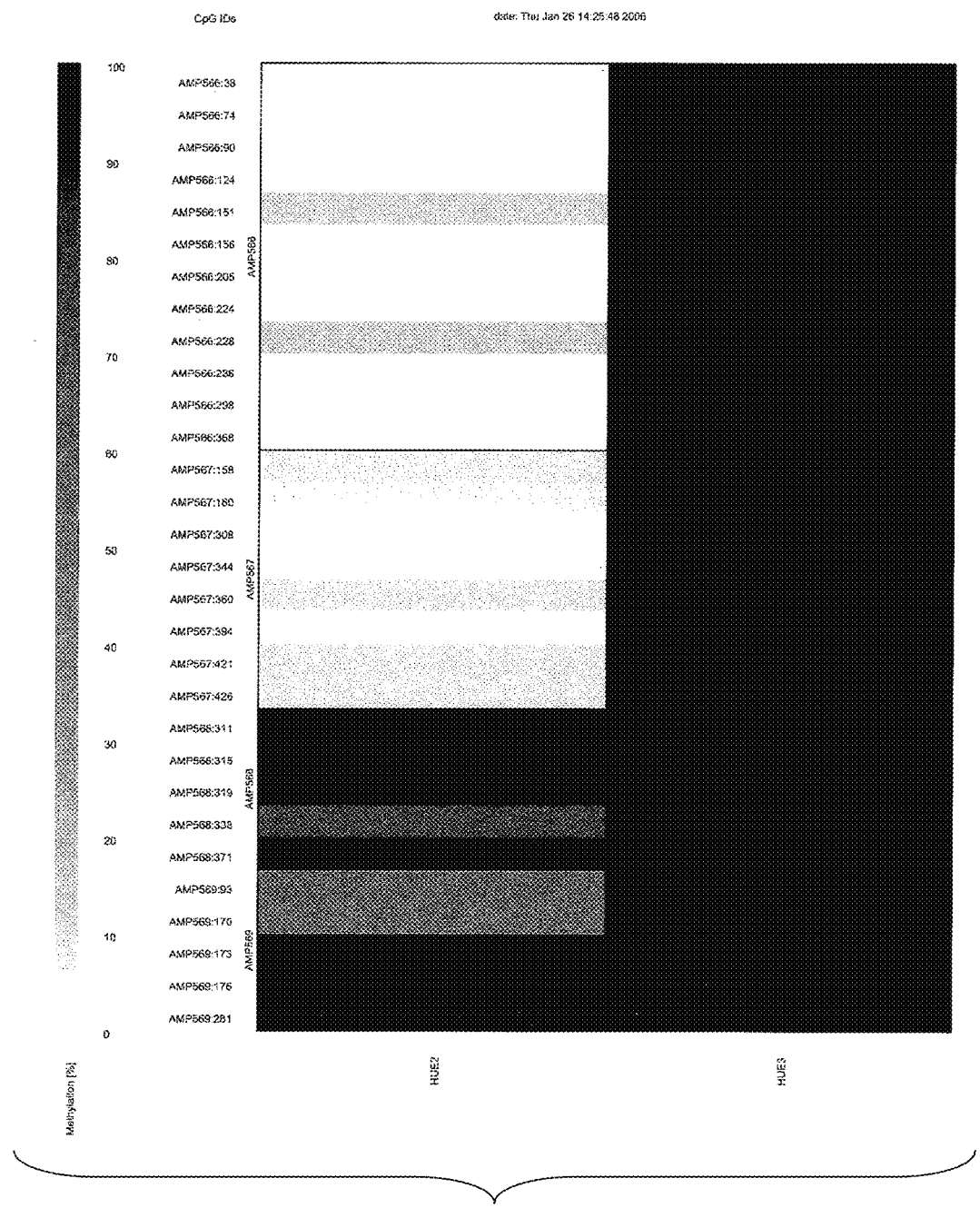
FIG. 3 shows the methylation analysis of purified lymphocytes, wherein the regulatory T-cell (HUE2 in FIG. 3) shows strong demethylation, in particular in amplicons 1 and 2 (all data ungrouped). AMP566=amplicon 2; AMP567=amplicon 1; AMP568=amplicon 4; and AMP569=amplicon 3. Particular positions in the amplicon are indicated by the number following the amplicon, i.e. AMP566:38 is position 38 in amplicon 2.

In one embodiment of the present invention, the methylation status of the Foxp3 locus was analyzed by bisulphite sequencing and revealed striking differences between CD25$^+$CD4$^+$ regulatory T cells and conventional CD25$^-$CD4$^+$ T cells. Amplicons 1 and 2 displayed a high degree of methylation (nearly 100%) within conventional CD25$^-$CD4$^+$ T cells, but were almost completely demethylated within CD25$^+$CD4$^+$ regulatory T cells (FIG. 3). No differences were observed for amplicons 3 and 4 showing that the demethylation process is not a random event, but confined to defined regions as was recently found for the IL-2 promoter (Bruniquel D, Schwartz R H. Selective, stable demethylation of the interleukin-2 gene enhances transcription by an active process. Nat Immunol. 2003 March; 4(3):235-40. Epub 2003 Jan. 27). Strikingly, a 384-bp stretch of the differentially methylated element, but not the region covered by amplicons 3 and 4 is highly conserved between mice and men (80.7% sequence identity), suggesting that functionally important parts are subject to epigenetic regulation. Furthermore, in silico analysis of the conserved region predicts a number of binding sites for transcription factors, including ATF/CREB, Elk-1, Ets-1, Evi-1, Foxp3, NFAT, NF-κB, SMAD-4 and STAT-1, suggesting that these factors might be involved in the induction of Foxp3-expression in $CD25^+$ $CD4^+$ regulatory T cells. The above region appears to be particularly involved in the regulation of foxp3, maybe in form of an alternative TATA-less promoter (the TATA box can be found upstream of the amplicons). Furthermore, there appears to be alternative splicing in the foxp3 gene (Genebank Accession number DQ010327). Only $CD25^+$ but not $CD25^-$ CD4 SP thymocytes displayed demethylated CpG motifs within the regions covered by amplicons 1 and 2. Again, CpGs in amplicons 3 and 4 were equally methylated. Interestingly, $CD25^+$ CD4 SP thymocytes showed a slightly reduced degree of demethylated DNA within amplicons 1 and 2 when compared to peripheral $CD25^+CD4^+$ regulatory T cells.

As expected, within cultured Th1 cells CpG motifs were completely methylated (FIG. 2B). In contrast, cell culture in the presence of TGF-β led to a demethylation of CpG motifs within the region covered by amplicons 1 and 2, although the degree of demethylation was less pronounced compared to $CD25^+$CD4 SP thymocytes or peripheral $CD25^+CD4^+$ regulatory T cells. Nevertheless, even in TGF-β-induced regulatory T cells the inventors could observe a correlation between demethylation of the conserved element and Foxp3 expression.

In conclusion, the demethylated status of the evolutionary conserved region upstream from exon −1 of foxp3 appears to be linked to a stable regulatory T cell phenotype. The findings suggest that a certain degree of CpG demethylation within this site is required to allow stable Foxp3 expression as was recently found for IL-2 (Bruniquel D, Schwartz R H. Selective, stable demethylation of the interleukin-2 gene enhances transcription by an active process. Nat Immunol. 2003 March; 4(3):235-40. Epub 27 Jan. 2003.). Therefore, determination of this parameter constitutes a more reliable marker for successful conversion of conventional T cells into regulatory T cells than the mere, temporary expression of Foxp3, as the latter, especially in the human system, has been detected also in activated, non-regulatory T cells (Ziegler S F. FOXP3: Of Mice and Men. Annu Rev Immunol., 1 Dec. 1005).

Based on the initial murine data, several amplicons covering candidate regions for differential DNA methylation of the human FOXP3 gene including putative regulatory elements were designed. Methylation analysis of the 11 amplicons was performed comparing human naïve CD25−CD45RA+CD4+ T cells with natural CD25highCD45RA−CD4+ Tregs from peripheral blood of three male donors (donors #1-3). Intracellular FOXP3 staining of FACS-sorted subsets revealed specific FOXP3 expression only in CD25highCD45RA−CD4+ Tregs (FIG. 5A), in accordance with findings from other labs (Walker M R, Kasprowicz D J, Gersuk V H, Benard A, Van Landeghen M, Buckner J H, Ziegler S F. Induction of FoxP3 and acquisition of T regulatory activity by stimulated human CD4+CD25− T cells. J Clin Invest. 2003; 112:1437-1443. Yagi H, Nomura T, Nakamura K, Yamazaki S, Kitawaki T, Hori S, Maeda M, Onodera M, Uchiyama T, Fujii S, Sakaguchi S. Crucial role of FOXP3 in the development and function of human CD25+CD4+ regulatory T cells. Int Immunol. 2004; 16:1643-1656. Roncador G, Brown P J, Maestre L, Hue S, Martinez-Torrecuadrada J L, Ling K L, Pratap S, Toms C, Fox B C, Cerundolo V, Powrie F, Banham A H. Analysis of FOXP3 protein expression in human CD4+CD25+ regulatory T cells at the single-cell level. Eur J Immunol. 2005; 35:1681-1691).

Figure 5B:
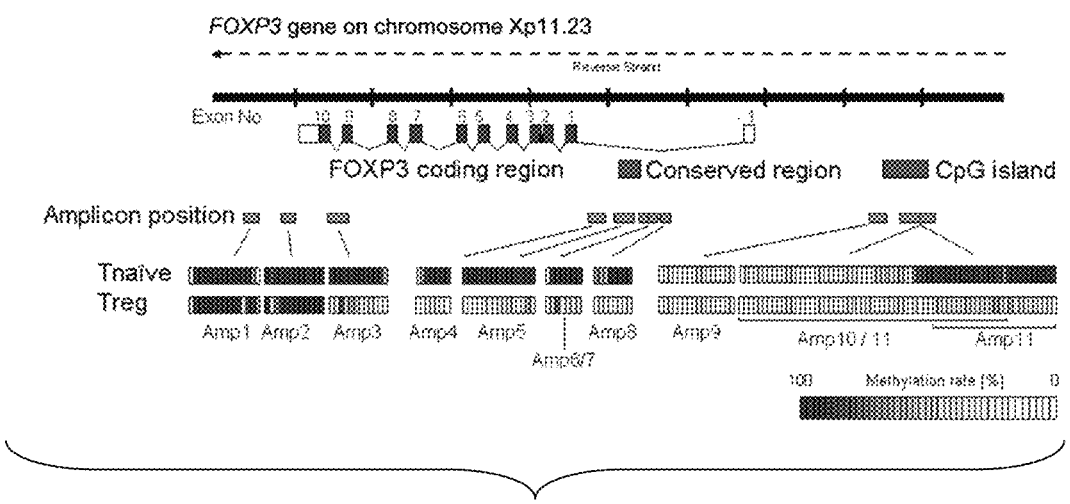

CpGs were found to be methylated in both cell types in the 3′ region of the gene (Amps 1 and 2 in FIG. 5B). Upstream of exon −1, CpGs in both cell types were demethylated up to the 5′ end of a CpG island (Amps 9 and 10). At the 5′ end of the FOXP3 gene, methylation was observed only in naïve CD4+ T cells, while tending towards demethylation in Tregs (Amps 10 and 11). Striking differences in the methylation pattern were observed within the gene body and putative promoter regions (Amps 3-8), in particular in a region highly conserved between mammals (Amp 5), for which we propose the name TSDR (Treg-specific demethylated region). To verify this finding, the inventors analyzed the methylation pattern of TSDR in another 12 donors (donors #4-15).

Figure 6:
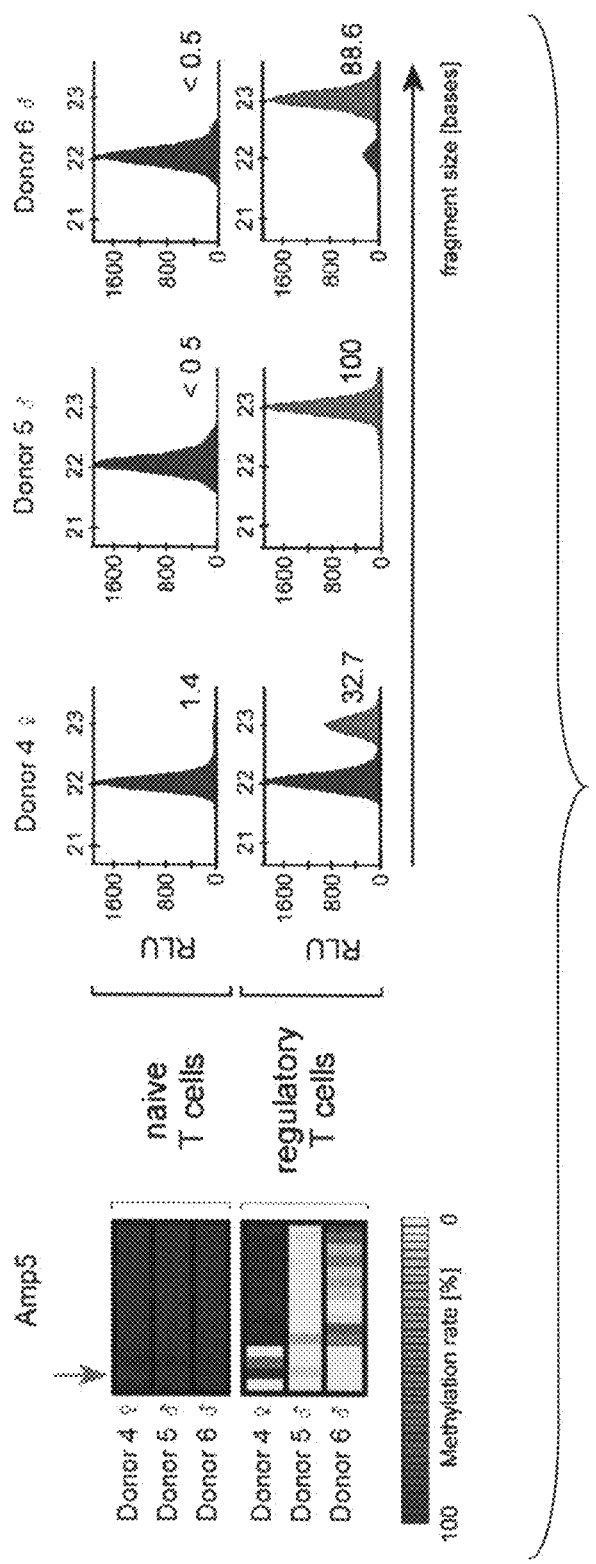
FIG. 6 shows the methylation pattern of the evolutionarily conserved region in Foxp3+$CD25^{high}$CD4+ Tregs. Methylation pattern of amplicon 5 (Amp5) covering the TSDR from donors #4-6 (left panel). A single CpG motif within Amp5 (red arrow) was selected for MS-SNuPE methylation-sensitive single-nucleotide primer extension) analysis, which was performed in the same three donors (right panel). Blue peaks correspond to a methylated cytosine and green peaks correspond to unmethylated cytosine. Original data are shown in the electropherogram (X-axis: fragment size in bases; Y-axis: signal intensities in relative light units). Numbers display frequency of unmethylated cytosines.

Since FOXP3 is X-linked, DNA from male and female donors was analyzed separately. In FIG. 6A, bisulfite sequencing of three donors, two male, one female, are shown (donors #4-6). As expected, the TSDR was fully methylated in naïve T cells from all donors (FIG. 6A). In Tregs derived from the two male donors (#5 and 6), the TSDR was fully demethylated, whereas Tregs derived from the female donor (#4) displayed hemimethylation. As a parallel approach, the methylation status of a single CpG motif within the TSDR was assayed by MS-SNuPE (methylation-sensitive single-nucleotide primer extension)-analysis in donors #4-15 (FIG. 6B, Table 1). This experiment confirmed the sequencing data since the inventors observed almost complete methylation of the selected CpG motif with a low background signal for all naïve CD25−CD45RA+CD4+ T cell samples. In contrast, this motif was always demethylated in male CD25highCD45RA−CD4+ Treg samples. Relative demethylation measured by MS-SNuPE corresponded to the percentage of FOXP3+ cells among CD25highCD45RA−CD4+ Tregs as determined by flow cytometry (Table 1). In females, the demethylation in all donors was approximately 50% of that of males with a given number of Foxp3+ cells, reflecting the epigenetic silencing of one allele of the X-chromosome.

To the inventors' knowledge, this is the first report of tissue-specific, epigenetic regulation of a gene that is subject to X-chromosome inactivation.

Transient FOXP3 expression in the absence of regulatory function has recently been reported for activated conventional CD4+ T cells (Morgan M E, van Bilsen J H, Bakker A M, Heemskerk B, Schilham M W, Hartgers F C, Elferink B G, van der Zanden, L de Vries R R, Huizinga T W, Ottenhoff T H, Toes R E. Expression of FOXP3 mRNA is not confined to CD4+CD25+ T regulatory cells in humans. Hum Immunol. 2005; 66:13-20. Gavin M A, Torgerson T R, Houston E, Deroos P, Ho W Y, Stray-Pedersen A, Ocheltree E L, Greenberg P D, Ochs H D, Rudensky A Y. Single-cell analysis of normal and FOXP3-mutant human T cells: FOXP3 expression without regulatory T cell development. Proc Natl Acad Sci USA. 2006; 103:6659-6664). To determine whether demethylation of the evolutionarily conserved region of the FOXP3 gene would occur in such transiently FOXP3 expressing CD4+ T cells, we stimulated FACS-sorted naïve CD25−CD45RA+CD4+ T cells for varying time points followed by flow cytometry analysis of FOXP3 expression and MSSNuPE-analysis of the methylation status of the FOXP3 gene.

The starting population of FACS-sorted naïve CD25−CD45RA+CD4+ T cells in general contained less then 0.5% FOXP3+ cells. However, upon stimulation, the cells not only uniformly upregulated both CD25 and FOXP3, but also expressed high levels of FOXP3 (FOXP3high) in a significant fraction of cells (FIG. 7, Table 2), confirming recently published data (Morgan M E, van Bilsen J H, Bakker A M, Heemskerk B, Schilham M W, Hartgers F C, Elferink B G, van der Zanden, L de Vries R R, Huizinga T W, Ottenhoff T H, Toes R E. Expression of FOXP3 mRNA is not confined to CD4+CD25+ T regulatory cells in humans. Hum Immunol. 2005; 66:13-20. Mantel P Y, Ouaked N, Ruckert B, Karagiannidis C, Welz R, Blaser K, Schmidt-Weber C B. Molecular mechanisms underlying FOXP3 induction in human T cells. J Immunol. 2006; 176:3593-3602. Gavin M A, Torgerson T R, Houston E, Deroos P, Ho W Y, Stray-Pedersen A, Ocheltree E L, Greenberg P D, Ochs H D, Rudensky A Y. Single-cell analysis of normal and FOXP3-mutant human T cells: FOXP3 expression without regulatory T cell development. Proc Natl Acad Sci USA. 2006; 103:6659-6664. Pillai V, Ortega S B, Wang C K, Karandikar N J. Transient regulatory T-cells: A state attained by all activated human T-cells. Clin Immunol. 2006; Epub ahead of print.)

When the inventors analyzed the methylation status of the FOXP3 gene in these activated CD4+ T cells by MS-SNuPE-analysis, we observed almost complete methylation of the selected CpG motif from the TSDR despite high FOXP3 expression (FIG. 7 and Table 2). Even in the case of one male donor depicted in FIG. 3, where almost 30% of the activated CD4+ T cells expressed high levels of FOXP3, hardly any demethylation (1.4%) was detectable by MSSN-uPE-analysis. This was not observed in total MACS-sorted CD4+ T cells, in which a fraction of 10.4% cells expressed FOXP3, largely composed of CD25highCD4+ Tregs. In contrast to the transiently FOXP3 expressing CD4+ T cells, these natural Tregs were easily detectable by MS-SNuPE-analysis as 12.7% demethylated CpG motifs were measured. Thus, the analysis of the methylation status of the FOXP3 gene allows discriminating between natural FOXP3+ CD25highCD4+ Tregs and conventional, non-regulatory CD4+ T cells only transiently expressing FOXP3 upon activation.

The bisulfite sequencing analysis of representative gene regions showed various differentially methylated regions including—but not limited to—the TSDR (Treg-specific demethylated region). As far as the TSDR is concerned, the data of freshly isolated naïve T cells and Tregs confirm previously reported murine data36, underlining the outstanding significance of this differentially methylated region.

The present invention shall now be further described in the following examples without being limited thereto.

Example I—Data Obtained with Mice

Mice

BALB/c mice were bred at the BfR (Bundesinstitut fuer Risikobewertung, Berlin, Germany) and used at 6-12 wk of age. All animal experiments were performed under specific pathogenfree conditions and in accordance with institutional, state and federal guidelines.

Ex vivo Cell Sorting

CD4+ T cells were isolated from pooled spleen and LN single cell suspensions by using anti CD4-FITC plus anti FITC multisort microbeads and the AutoMACS magnetic separation system (Miltenyi Biotec). After release of beads according to the manufacturer's instructions, CD25+ and CD25− cells were separated using anti CD25-APC plus anti APC microbeads. Thymic single cell suspensions were sorted for CD8+ and CD8− cells using anti CD8 microbeads and the AutoMACS magnetic separation system. MACS-sorted CD8− thymocytes were subsequently stained using anti CD4-FITC, anti CD25-APC and anti CD19−PE and sorted into CD25+ and CD25− subsets of CD4 SP thymocytes as well as into CD19− DN thymocytes by FACS (Aria, BD Bioscience). MACS-sorted CD8+ thymocytes were stained using anti CD4-FITC and anti CD8-PerCP and sorted into DP thymocytes by FACS. All subsets were sorted to a purity of >98%.

TGF-β-Induced Regulatory T Cells

CD4+ T cells were isolated from pooled spleen and LN single cell suspensions by using anti CD4-FITC plus anti FITC multisort microbeads and the AutoMACS magnetic separation system (Miltenyi Biotec). After release of beads according to the manufacturer's instructions, CD25+ cells were depleted by using anti CD25−APC plus anti APC microbeads. To avoid the expansion of precommitted Foxp3+ regulatory T cells the inventors excluded the majority of residual Foxp3+ regulatory T cells from the CD25− CD4+ T cell fraction by sorting for CD62Lhigh cells using anti CD62L microbeads. MACS-sorted CD62LhighCD25− CD4+ T cells were stimulated for 2 days using plate bound anti CD3 (6 µg/ml) and anti CD28 (4 µg/ml). For Th1 cultures 5 µg/ml anti-IL-4, 20 ng/ml IFN-γ (R&D systems) and 5 ng/ml IL-12 (R&D systems) and for TGF-β cultures 5 ng/ml TGF-β (Sigma) and 10 ng/ml IL-2 (R&D systems) was added to the culture. After 2 days cells were removed from the stimulus, transferred to non-coated plates and cultured for another 3 days. All cell culture was done with RPMI 1640 (Gibco) supplemented with 10% FCS (Sigma). On day 5, cultured cells were stained using anti CD25-APC and sorted for CD25+ cells by FACS (Aria).

Methylation Analyses Protocol:

Focusing on a 30.8 kb region of the sf locus (Brunkow M E et al. (2001) Nat Gen. 27:68) harboring the foxp3 gene, sequences for methylation analysis was selected based on the CpG density. In particular, promoter regions as well as exon intron borders were considered for amplicon design. Upon PCR, primers were designed to produce four amplicons: Overlapping amplicons 1 and 2 map upstream of the transcriptional start site, amplicon 3 and 4 align to the 7th intron according to Brunkow et al (Brunkow M E et al (2001) Nat Gen. 27:68).

Primers (5' to 3' direction) for the four amplicons and their exact genomic location according to ENSEMBL (v36 December 05) are summarized:

```
Amp 566 (amplicon 2): X 5822854 to 5823308 (+)
fw:    ATTTGAATTGGATATGGTTTGT      (SEQ ID NO: 1);
rev:   AACCTTAAACCCCTCTAACATC      (SEQ ID NO:. 2);

Amp567 (amplicon 1): X 5822584 to 5823048 (+)
fw:    AGGAAGAGAAGGGGGTAGATA       (SEQ ID NO: 3);
rev:   AAACTAACATTCCAAAACCAAC      (SEQ ID NO: 4);

AMP568 (amplicon 4): X 5829352 to 5829652 (+)
fw:    TGGTTGTTTTGGAGTTTAGTGT      (SEQ ID NO: 5);
rev:   CACTTTTCTACCTTCCACAAAT      (SEQ ID NO: 6);
```

-continued

Amp569 (amplicon 3): X 5828765 to 5829243 (+)
fw: AGAGGTTGAAGGAGGAGTATTT (SEQ ID NO: 7);
rev: ACTATCTATCCAATTCCCCAAC (SEQ ID NO: 8).

The primers were used for both PCR amplification of bisulfite converted genomic DNA and sequence reactions.

Genomic DNA was isolated from purified lymphocytes using the DNeasy tissue kit (Qiagen, Hilden, Germany) following the supplier's recommendations.

Sodium bisulfite treatment of genomic DNA was performed according to Olek et al. (Olek, A., Oswald, J., Walter, J. (1996) Nucleic Acids Res. 24, 5064-5066) with minor modifications, resulting in the conversion of unmethylated cytosine to uracil, whereas methylated cytosines remain unchanged. In a subsequent PCR amplification uracil is replaced by thymine. Thus, detection of a "C" in sequencing reactions reflects methylation of the genomic DNA at that site. Detection of a "T" at the same site instead, reflects the absence of a methyl modification of the genomic cytosine.

PCRs were performed on MJ Research thermocyclers (Waltham, Mass., United States) in a final volume of 25 μl containing 1×PCR Buffer, 1 U Taq DNA polymerase (Qiagen, Hilden, Germany), 200 μM dNTPs, 12.5 pmol each of forward and reverse primers, and 7 ng of bisulfite-treated genomic DNA. The amplification conditions were 95° C. for 15 min and 40 cycles of 95° C. for 1 min., 55° C. for 45 sec and 72° C. for 1 min. and a final extension step of 10 min. at 72° C. PCR products were purified using ExoSAP-IT (USB Corp., Cleveland, Ohio, United States) and sequenced applying the PCR primer(s) and the ABI Big Dye Terminator v1.1 cycle sequencing chemistry (Applied Biosystems, Foster City, Calif., United States) followed by capillary electrophoresis on an ABI 3100 genetic analyzer. Trace files were interpreted using ESME, which normalizes sequence traces, corrects for incomplete bisulfite conversion and allows for quantification of methylation signals (Lewin, J., Schmitt, A. O., Adorjan, P., Hildmann, T., Piepenbrock, C. (2004) Bioinformatics. 20, 3005-3012).

Example II—Data Obtained with Humans

Cell Preparation and Flow Cytometry

Buffy coats were obtained in accordance with local ethical committee approval (DRK Blutspendedienst, Berlin, Germany). PBMCs were separated with a Ficoll-Hypaque gradient (Sigma-Aldrich). The purity of the sorted population was 95-99%, as determined by FACScalibur™ using CELLQest™ Software (BDBiosciences). CD4+ T cells were isolated from PBMCs by using anti-CD4 microbeads and the AutoMACS magnetic separation system (Miltenyi Biotec). MACS-sorted CD4+ T cells were stained using anti-CD45RA-FITC and anti-CD25-APC (MA-251, BD-PharMingen). Cells were sorted into CD25highCD45RA− Tregs and CD25−CD45RA+ naïve T cells by FACS (Aria, BD-Bioscience). FOXP3 staining was performed with the PE anti-human FOXP3 staining set (eBioscience). Cytometric analysis was performed on a LSRII (BD-Biosciences) using the CellQuest™ software.

In vitro Stimulation of Naïve CD4+ T Cells

FACS-sorted naïve CD4+ T cells (CD25−CD45RA+) were stimulated for three to seven days using antiCD3/antiCD28-coated beads (Dynal) according to the manufacturers instructions. Cell culture was performed in RPMI medium (Gibco) supplemented with 10% FCS (Sigma). On indicated time points, stimulated cells were harvested and aliquots were taken for both the analysis of FOXP3 expression by flow cytometry and for the analysis of the methylation status of the FOXP3 gene.

DNA Preparation, Bisulphite Conversion, PCR and Sequencing

Genomic DNA was isolated using the DNeasy tissue kit (Qiagen) following the protocol for cultured animal cells. Bisulfite treatment of genomic DNA was performed as previously described (Olek A, Oswald J, Walter J. A modified and improved method for bisulphite based cytosine methylation analysis Nucleic Acids Res. 2007; 24:5064-5066.). PCRs were performed in a final volume of 25 μl containing 1×PCR Buffer, 1 U Taq DNA polymerase (Qiagen), 200 μM dNTPs, 12.5 pmol each of forward and reverse primers, and 7 ng of bisulphite-treated genomic DNA at 95° C. for 15 min and 40 cycles of 95° C. for 1 min, 55° C. for 45 sec and 72° C. for 1 min and a final extension step of 10 min at 72° C. PCR products were purified using ExoSAP-IT (USB Corp.) and sequenced applying the PCR primers and the ABI Big Dye Terminator v1.1-chemistry (Applied Biosystems) followed by capillary electrophoresis on an ABI 3100 genetic analyzer. ABI files were interpreted using ESME (Lewin J, Schmitt A O, Adorjan P, Hildmann T, Piepenbrock C. Quantitative DNA methylation analysis based on four-dye trace data from direct sequencing of PCR amplificates. Bioinformatics. 2004; 20:3005-3012.).

Oligonucleotides

Sequences are given in 5' to 3' direction. Primers were used for bisulfite-specific PCR and sequence reactions. Strand specificity and orientation: Primers "p" and "o" produce amplicons based on the +1 strand, "r" and "q" on the −1 strand. Primers "p" and "q" indicated forward, primers "o" and "p" denote reverse orientation.

| Amplificate | Sequence | Sequence |
|---|---|---|
| Amp1 | p-GTTATTTGTGGAGTTTTATGGG (SEQ ID NO: 9) | o-CCCCACTACTTACCTCTCTACA (SEQ ID NO:10) |
| Amp2 | r-AAAACCCTCCTATCTACCTCC (SEQ ID NO: 11) | q-AGGGTATGTGTTTGGTTATTGT (SEQ ID NO:12) |
| Amp3 | r-AAACCTCACTTCTTAATCCCTA (SEQ ID NO: 13) | q-TTGGGATGGTTTTAAGTGTTAT (SEQ ID NO: 14) |
| Amp4 | r-AACCCTCAAACCTAACTCATAC (SEQ ID NO: 15) | q-GGAGGTGATAGTAAAGAAAGGA (SEQ ID NO: 16) |
| Amp5 | p-TGTTTGGGGGTAGAGGATTT (SEQ ID NO: 17) | o-TATCACCCCACCTAAACCAA (SEQ ID NO: 18) |

-continued

| Amplificate | Sequence | Sequence |
|---|---|---|
| Amp6 | r-AAATCCTAAAATCTCAAAACCA (SEQ ID NO: 19) | q-GGTGATGATGGAGGTATGTTA (SEQ ID NO: 20) |
| Amp7 | p-TAGAGATGGTAATAGGGGAG (SEQ ID NO: 21) | o-CCAACCTCACAAAAACTAAACT (SEQ ID NO: 22) |
| Amp8 | p-GTGAGGTTGGGTTTTATATTGT (SEQ ID NO: 23) | o-TATCCCTATCTCTCAACCAATC (SEQ ID NO: 24) |
| Amp9 | r-TCCTAATTCACACACCAAAATA (SEQ ID NO: 25) | q-AAGGTTAAAAGGAGATTAAGAGG (SEQ ID NO: 26) |
| Amp10 | r-AATTTTACCTAATCCCCACATT (SEQ ID NO: 27) | q-GGTTGTTGGTTTAGAAAGTGTT (SEQ ID NO: 28) |
| Amp11 | p-AGGAGTAGGAGATTTTATTTTGG (SEQ ID NO: 29) | o-TTCAACTACCTAACCTCAACCT (SEQ ID NO: 30) |

MS-SNuPE

MS-SNuPE was performed using the ABIPrism-Snapshot kit (Applied Biosystems). Substrates were PCR products produced from bisulphite-converted genomic DNA using primers Amp5 "p" and "o". The assay utilizes internal extension primer(s) annealing immediately 5' of the relevant nucleotide. In presence of labelled ddNTPs, the primer is extended by a single nucleotide. Capillary Electrophoresic analysis was performed by using ABI 3100 Genetic Analyzer and GeneMapper software (v3.5). Extension primers: FOXP3: CCCAACAAACAATACAAAAAACC (SEQ ID NO: 31).

TABLE 1

Demethylation of the FOXP3 gene in CD25highCD4+ Tregs corresponds to frequency of FOXP3+ cells.

| Donor | MS-SNuPE [% non-methylated] | FACS [% FOXP3+ cells] | Gender |
|---|---|---|---|
| 4 | 32.7 | 71.3 | F |
| 5 | 100.0 | 95.1 | M |
| 6 | 88.6 | 89.9 | M |
| 7 | 84.3 | 84.9 | M |
| 8 | 100.0 | 88.7 | M |
| 9 | 93.6 | 82.9 | M |
| 10 | 84.3 | 92.0 | M |
| 11 | 45.7 | 95.6 | F |
| 12 | 38.4 | 79.6 | F |
| 13 | 33.9 | 85.9 | F |
| 14 | 50.0 | 76.9 | F |
| 15 | 88.0 | 94.6 | M |

Summary of MS-SNuPE and flow cytometry analysis of FACS-sorted CD25highCD45RATregs from twelve donors (#4-15). MS-SNuPE analysis was performed as described in FIG. 6. Frequencies of unmethylated cytosins and frequencies of FOXP3+ cells within CD25highCD45RA− Tregs from male (M) and female (F) donors are depicted.

TABLE 2

Methylated FOXP3 gene in activated conventional FOXP3+CD4+ T cells.

| Donor | Culture duration [days] | MS-SNuPE [% non-methylated] | FACS [% FOXP3high cells] | Gender |
|---|---|---|---|---|
| 16 | 3 | 1.6 | 12.4 | F |
| 17 | 3 | 1.6 | 14.5 | M |
| 17 | 4 | 1.4 | 29.7 | M |
| 18 | 3 | 1.5 | 14.2 | M |
| 19 | 3 | 3.9 | 12.8 | M |
| 20 | 4 | 1.7 | 39.3 | F |
| 20 | 7 | 3.9 | 32.5 | F |

Summary of MS-SNuPE and flow cytometry analysis of in vitro stimulated naive CD4+ T cells from five donors. Cells were stimulated for varying time points. MS-SNuPE analysis was performed essentially as described in FIG. 3. Frequencies of unmethylated cytosins and frequencies of FOXP3$^{high}$ cells within stimulated T cells from male (M) and female (F) donors are depicted.

It should be understoood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of identifying stable FoxP3 positive regulatory T cells and treating a disease in a human subject, the method comprising:
   a) obtaining a sample containing human regulatory T cells from a donor or a cell culture;
   b) identifying stable FoxP3 positive human regulatory T cells from a portion of the sample comprising:
      i) isolating genomic DNA from the portion of the sample;
      ii) treating the isolated genomic DNA with bisulfite to convert unmethylated cytosines to uracils;
      iii) amplifying the treated isolated genomic DNA by polymerase chain reaction (PCR) using a pair of oligonucleotide primers comprising SEQ ID NO: 13 and SEQ ID NO: 14, or SEQ ID NO: 15 and SEQ ID NO: 16, or SEQ ID NO: 17 and SEQ ID NO: 18, or SEQ ID NO: 29 and SEQ ID NO: 30 to produce an amplicon;
      iv) sequencing the amplicon; and
      v) analyzing the amplicon for a lack of methylation at cytosine phosphate guanine (CpG) positions in the human FoxP3 gene in the amplicon, wherein a lack of methylation at the CpG positions is indicative of stable FoxP3 positive human regulatory T cells in the sample; and
   c) administering a portion of the sample from step a), wherein the sample contains stable FoxP3 positive human regulatory T cells as identified in step b) to thereby treat an autoimmune disease, adverse effects in allotransplant recipients, tumorous diseases, allergic asthma, ovarian cancer, chronic graft-versus host disease, multiple sclerosis, or immunodysregulation polyendocrinopathy enteropathy X-linked (IPEX) syndrome in the human subject.

2. The method according to claim 1, further comprising inducing the cells in said sample with transforming growth factor-β (TGF-β).

3. The method according to claim 1, further comprising identifying said FoxP3-positive human regulatory T cell as a CD25+CD4+ T cell.

4. The method according to claim 1, wherein said oligonucleotide primers SEQ ID NO:13 and SEQ ID NO:14 are used to amplify said treated genomic DNA.

5. The method according to claim 1, wherein said oligonucleotide primers SEQ ID NO:15 and SEQ ID NO:16 are used to amplify said treated genomic DNA.

6. The method according to claim 1, wherein said oligonucleotide primers SEQ ID NO:17 and SEQ ID NO:18 are used to amplify said treated genomic DNA.

7. The method according to claim 1, comprising amplifying the treated isolated genomic DNA by PCR using a pair of oligonucleotide primers comprising.

8. The method according to claim 1, wherein the portion of the sample from step a) administered to the human subject is further identified as CD25+CD4+ T cells.

9. The method according to claim 1, wherein the pair of oligonucleotide primers consist of SEQ ID NO: 13 and SEQ ID NO: 14.

10. The method according to claim 1, wherein the pair of oligonucleotide primers consist of SEQ ID NO: 15 and SEQ ID NO: 16.

11. The method according to claim 1, wherein the pair of oligonucleotide primers consist of SEQ ID NO: 17 and SEQ ID NO: 18.

12. The method according to claim 1, wherein the pair of oligonucleotide primers consist of SEQ ID NO:29 and SEQ ID NO:30.

* * * * *